United States Patent
Ushikura et al.

(10) Patent No.: US 11,612,366 B2
(45) Date of Patent: Mar. 28, 2023

(54) RADIATION DETECTOR, RADIOGRAPHY APPARATUS, AND METHOD OF MANUFACTURING RADIATION DETECTOR

(71) Applicant: FUJIFILM Corporation, Tokyo (JP)

(72) Inventors: Shinichi Ushikura, Kanagawa (JP); Munetaka Kato, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 205 days.

(21) Appl. No.: 17/176,429

(22) Filed: Feb. 16, 2021

(65) Prior Publication Data
US 2021/0259650 A1    Aug. 26, 2021

(30) Foreign Application Priority Data

Feb. 20, 2020 (JP) .............................. JP2020-027528

(51) Int. Cl.
*A61B 6/00* (2006.01)
*G01T 1/20* (2006.01)

(52) U.S. Cl.
CPC .......... *A61B 6/4208* (2013.01); *G01T 1/2018* (2013.01)

(58) Field of Classification Search
None
See application file for complete search history.

(56) References Cited

U.S. PATENT DOCUMENTS

| 11,428,827 B2* | 8/2022 | Ushikura .............. G01T 1/1612 |
| 2019/0221602 A1* | 7/2019 | Komai ................. H01L 27/1469 |
| 2020/0408930 A1 | 12/2020 | Ushikura et al. |

FOREIGN PATENT DOCUMENTS

| JP | 2004-296656 A | 10/2004 |
| JP | 2006-148005 A | 6/2006 |
| JP | 2014-081363 A | 5/2014 |
| WO | 2019/181569 A1 | 9/2019 |
| WO | 2019/181639 A1 | 9/2019 |

OTHER PUBLICATIONS

An Office Action; "Notice of Reasons for Refusal," mailed by the Japanese Patent Office dated Oct. 25, 2022, which corresponds to Japanese Patent Application No. 2020-027528 and is related to U.S. Appl. No. 17/176,429; with English language translation.

* cited by examiner

*Primary Examiner* — Edwin C Gunberg
(74) *Attorney, Agent, or Firm* — Studebaker & Brackett PC

(57) ABSTRACT

The radiation detector includes a sensor substrate and a reinforcing substrate. In the sensor substrate, a plurality of pixels for accumulating the charges generated according to light converted from radiation are formed in the pixel region on the first surface of the flexible base material, and the terminal for electrically connecting a flexible cable to the first surface is provided. The reinforcing substrate is provided on the second surface opposite to the first surface of the base material in a region excluding at least the facing region facing the terminal to reinforce the stiffness of the base material.

16 Claims, 16 Drawing Sheets

RADIATION DETECTOR, RADIOGRAPHY APPARATUS, AND METHOD OF MANUFACTURING RADIATION DETECTOR

CROSS-REFERENCE TO RELATED APPLICATIONS

The present application claims priority under 35 U.S.C. § 119 to Japanese Patent Application No. 2020-027528 filed on Feb. 20, 2020. The above application is hereby expressly incorporated by reference, in its entirety, into the present application.

BACKGROUND

1. Technical Field

The present invention relates to a radiation detector, a radiography apparatus, and a method of manufacturing the radiation detector.

2. Description of the Related Art

Conventionally, a radiography apparatus for performing radiography for the purpose of medical diagnosis has been known. In such a radiography apparatus, a radiation detector for detecting radiation that has transmitted through a subject and generating a radiographic image is used.

The radiation detector comprises a conversion layer such as a scintillator for converting radiation into light, and a substrate provided with a plurality of pixels for accumulating charges generated according to the light converted by the conversion layer. As a base material for a sensor substrate of such a radiation detector, a base material using a flexible base material is known. By using the flexible base material, the radiography apparatus can be made lightweight, and imaging of a subject may be facilitated.

In a case where a load or an impact is applied to the radiography apparatus, a substrate using the flexible base material is easily bent, so that a technique of increasing a bending stiffness of the radiation detector is known in order to suppress the influence of the impact on the radiation detector. For example, in the technique disclosed in JP2004-296656A, a photoelectric conversion substrate and a supporting member are fixed by a bonding member in a region other than a connection portion between an electric component and the photoelectric conversion substrate on an outer peripheral portion of the photoelectric conversion substrate. In addition, for example, in the technique disclosed in JP2014-081363A, a technique in which a reinforcing substrate is attached to a radiation incident side of a photoelectric conversion panel or to a side opposite to the radiation incident side has been described. Further, for example, in the technique disclosed in WO2019/181569A, a reinforcing substrate is provided on at least one of a surface on the substrate side or a surface on the conversion layer side of a laminate in which the base material and the conversion layer are laminated.

SUMMARY

By the way, in a case where the cable is electrically connected to a terminal, it is desired to reinforce a bending stiffness of the base material in the vicinity of the terminal. On the other hand, in a case where the cable is electrically connected to the terminal, heat applied to the terminal is applied to the base material by heat treatment or the like for connection, and the heat is propagated to the reinforcing substrate. In some cases, the reinforcing member is deformed by heat propagated from the terminal.

An object of the present disclosure is to provide the radiation detector, the radiography apparatus, and the method of manufacturing the radiation detector, which have high bending stiffness and suppress the deformation of the reinforcing substrate due to heat applied to the terminal.

In order to achieve the above object, a radiation detector according to the first aspect of the present disclosure comprises a substrate in which a plurality of pixels for accumulating charges generated according to light converted from radiation are formed in a pixel region on the first surface of a flexible base material, and a terminal for electrically connecting a cable is provided on the first surface, and a reinforcing substrate that is provided in a region of a second surface opposite to the first surface of the base material, excluding at least a facing region facing the terminal, to reinforce a stiffness of the base material.

In the radiation detector according to the second aspect of the present disclosure, in the radiation detector according to the first aspect, the reinforcing substrate is provided with a cutout portion at a position including the facing region.

In the radiation detector according to the third aspect of the present disclosure, in the radiation detector according to the first aspect, the reinforcing substrate is provided with a gap portion at a position including the facing region.

In the radiation detector according to the fourth aspect of the present disclosure, in the radiation detector according to the first aspect, the reinforcing substrate is provided in a region extending to at least a part of a side provided with the terminal of the base material.

In the radiation detector according to the fifth aspect of the present disclosure, in the radiation detector according to the first aspect, the substrate is provided with a plurality of the terminals, and the reinforcing substrate is also provided in a region corresponding to a portion between the plurality of terminals.

In the radiation detector according to the sixth aspect of the present disclosure, in the radiation detector according to the first aspect, the reinforcing substrate is provided in a region including the facing region, and excluding at least a region in which heat that causes a deformation amount of the reinforcing substrate to be a predetermined amount or more is applied to the base material in a heat treatment performed in a case where the cable is electrically connected to the terminal.

In the radiation detector according to the seventh aspect of the present disclosure, in the radiation detector according to the first aspect, a bending stiffness of the reinforcing substrate is higher than that of the base material.

In the radiation detector according to the eighth aspect of the present disclosure, in the radiation detector according to the first aspect, a bending stiffness of the reinforcing substrate is 540 $Pacm^4$ or more and 140,000 $Pacm^4$ or less.

The radiation detector according to the ninth aspect of the present disclosure further comprises, in the radiation detector according to the first aspect, a conversion layer that converts the radiation into light, which is provided in a region including the pixel region on the first surface of the substrate and excluding a region in which the terminal is provided, and the reinforcing member provided on a surface of the conversion layer, which is opposite to a surface on the base material side.

A radiography apparatus according to the tenth aspect of the present disclosure comprises the radiation detector claimed in the first aspect, and a circuit unit for reading the charges accumulated in the plurality of pixels.

A method of manufacturing a radiation detector according to the eleventh aspect of the present disclosure comprises a forming a substrate in which a flexible base material is provided on a support, a plurality of pixels for accumulating charges generated according to light converted from radiation are provided in a pixel region on the first surface of the base material, and a terminal for electrically connecting a cable is provided on the first surface, and a providing a reinforcing substrate for reinforcing a stiffness of the base material in a region of a second surface opposite to the first surface of the base material, excluding at least a facing region facing the terminal.

The method of manufacturing the radiation detector according to the twelfth aspect of the present disclosure further comprises, in the method of manufacturing the radiation detector according to the eleventh aspect, an electrically connecting the cable to the terminal after providing the reinforcing substrate.

The method of manufacturing the radiation detector according to the thirteenth aspect of the present disclosure further comprises, in the method of manufacturing the radiation detector according to the eleventh aspect, a providing a replenishing member having a smaller deformation amount with respect to heat than that of the reinforcing substrate in a region in which the reinforcing substrate is not provided on the second surface of the base material, and an electrically connecting the cable to the terminal after providing the reinforcing substrate and the replenishing member.

The method of manufacturing the radiation detector according to the fourteenth aspect of the present disclosure further comprises, in the method of manufacturing the radiation detector according to the eleventh aspect, a providing a replenishing member having a higher thermal conductivity than that of the reinforcing substrate in a region in which the reinforcing substrate is not provided on the second surface of the base material, and an electrically connecting the cable to the terminal after providing the reinforcing substrate and the replenishing member.

The method of manufacturing the radiation detector according to the fifteenth aspect of the present disclosure further comprises, in the method of manufacturing the radiation detector claimed in the thirteenth aspect, a removing the replenishing member after electrically connecting the cable to the terminal.

The method of manufacturing the radiation detector according to the sixteenth aspect of the present disclosure further comprises, in the method of manufacturing the radiation detector claimed in the fourteenth aspect, a removing the replenishing member after electrically connecting the cable to the terminal.

According to the present disclosure, the bending stiffness is high, and the deformation of the reinforcing substrate due to the heat applied to the terminal can be suppressed.

BRIEF DESCRIPTION OF THE DRAWINGS

Exemplary embodiments according to the technique of the present disclosure will be described in detail based on the following figures, wherein.

DETAILED DESCRIPTION

Hereinafter, embodiments of the present invention will be described in detail with reference to the drawings. It should be noted that the embodiment does not limit the present invention.

First Embodiment

A radiation detector of the present embodiment has a function of detecting radiation that has transmitted through a subject and outputting image information representing a radiographic image of the subject. The radiation detector of the present embodiment comprises a sensor substrate and a conversion layer for converting radiation into light (refer to FIG. 3A and FIG. 3B, and a sensor substrate 12 and a conversion layer 14 of a radiation detector 10). The sensor substrate 12 of the present embodiment is an example of the substrate of the present disclosure.

Figure 1:
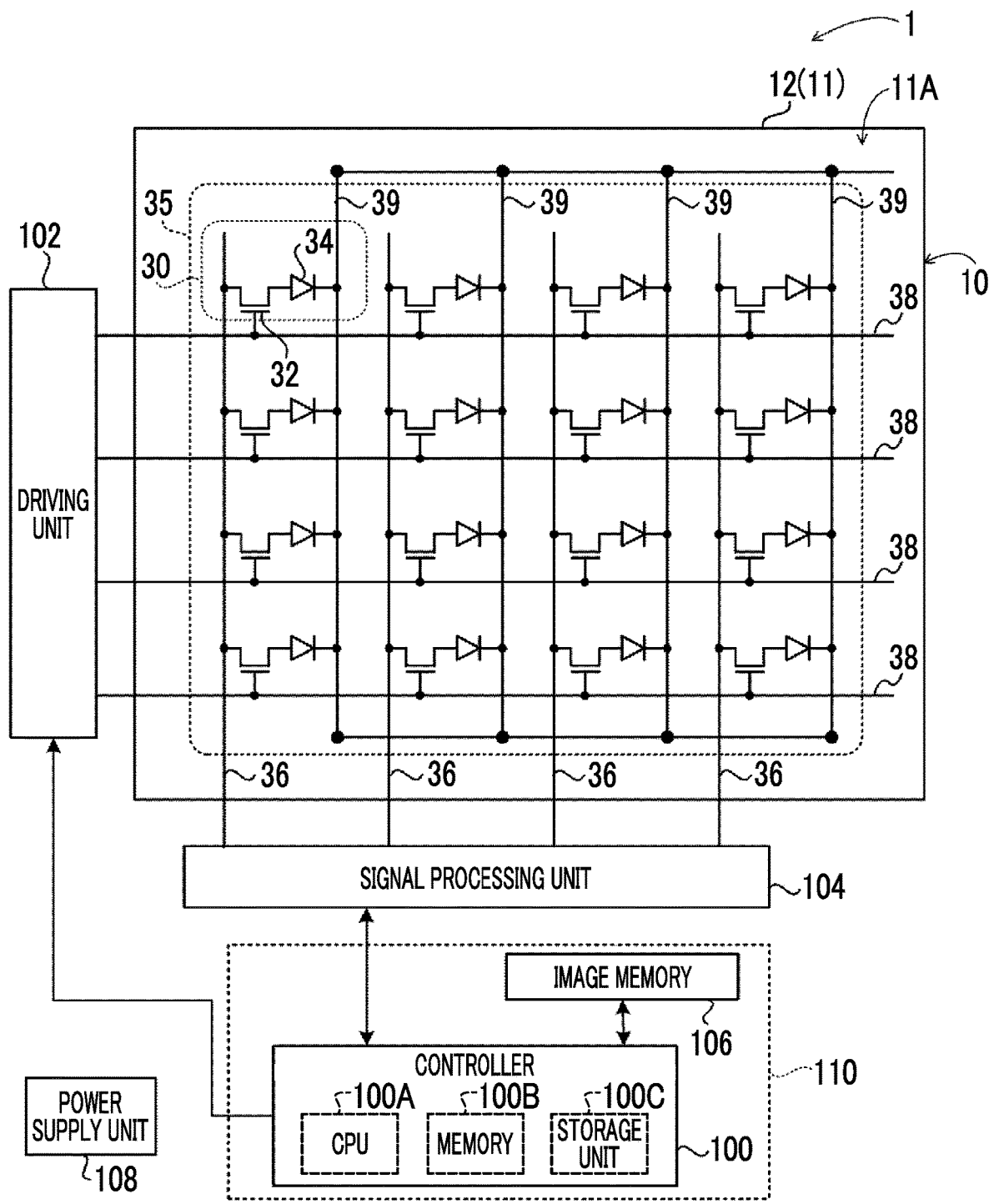
FIG. 1 is a block diagram showing an example of a main configuration of an electrical system in a radiography apparatus according to an embodiment.

First, with reference to FIG. 1, a schematic description of an example of a configuration of an electrical system in the radiography apparatus of the present embodiment will be described. FIG. 1 is a block diagram showing an example of a main configuration of an electrical system in a radiography apparatus according to an present embodiment.

As shown in FIG. 1, a radiography apparatus 1 of the present embodiment comprises a radiation detector 10, a controller 100, a driving unit 102, a signal processing unit 104, an image memory 106, and a power supply unit 108. At least one of the controller 100, the driving unit 102, or the signal processing unit 104 of the present embodiment is an example of a circuit unit of the present disclosure. Hereinafter, in a case where the controller 100, the driving unit 102, and the signal processing unit 104 are collectively referred to as a "circuit unit".

The radiation detector 10 comprises the sensor substrate 12 and the conversion layer 14 (refer to FIG. 3A and FIG. 3B) that converts radiation into light. The sensor substrate 12 comprises a flexible base material 11 and a plurality of pixels 30 provided on the first surface 11A of the base material 11. Hereinafter, the plurality of pixels 30 may be simply referred to as "pixel 30".

As shown in FIG. 1, each pixel 30 of the present embodiment comprises a sensor portion 34 that generates and accumulates charges according to light converted by the conversion layer, and a switching element 32 that reads the charges accumulated in the sensor portion 34. In the present embodiment, as an example, a thin film transistor (TFT) is used as the switching element 32. Therefore, the switching element 32 will be referred to as "TFT 32" below. In the present embodiment, a sensor portion 34 and the TFT 32 are formed, and a layer having the pixels 30 is provided as a planarized layer on the first surface 11A of the base material 11.

The pixels 30 are disposed two-dimensionally in the pixel region 35 of the sensor substrate 12 along one direction (a scanning wiring direction corresponding to a lateral direction of FIG. 1, hereinafter also referred to as "row direction") and an cross direction with respect to a row direction (a signal wiring direction corresponding to a machine direction of FIG. 1, hereinafter also referred to as "column direction"). In FIG. 1, an arrangement of the pixels 30 is simplified, but for example, the pixels 30 are disposed in the row direction and the column direction by 1024 px×1024 px.

The radiation detector 10 is provided with a plurality of scanning wirings 38 comprised for each row of the pixels 30 for controlling a switching state (on and off) of the TFT 32, and a plurality of signal wirings 36 comprised for each column of the pixels 30 for reading charges accumulated in the sensor portion 34, crossing each other. Each of the plurality of scanning wirings 38 is connected via a flexible cable 112A to the driving unit 102, so that the driving signal output from the driving unit 102 and driving the TFT32 to control the switching state flows to each of the plurality of scanning wirings 38. In addition, each of the plurality of signal wirings 36 is connected to the signal processing unit 104 via the flexible cable 112B, so that the charges read from each pixel 30 are output to the signal processing unit 104 as an electric signal. The signal processing unit 104 generates and outputs image data according to the input electric signal. In the present embodiment, the term "connection" with respect to the flexible cable 112 means electrical connection.

A controller 100 described later is connected to the signal processing unit 104, and the image data output from the signal processing unit 104 is sequentially output to the controller 100. The controller 100 is connected to the image memory 106, and the image data sequentially output from the signal processing unit 104 is sequentially stored in the image memory 106 under the control of the controller 100. The image memory 106 has a storage capacity capable of storing a predetermined number of image data, and the image data obtained by imaging are sequentially stored in the image memory 106 each time the radiographic image is captured.

The controller 100 comprises a central processing unit (CPU) 100A, a memory 100B including a read only memory (ROM) and a random access memory (RAM), and a non-volatile storage unit 100C such as a flash memory. As an example of the controller 100, a microcomputer or the like can be included. The controller 100 controls the entire operation of the radiography apparatus 1.

It should be noted that in the radiography apparatus 1 according to the present embodiment, the image memory 106, the controller 100, and the like are formed on a control substrate 110.

In addition, the sensor portion 34 of each pixel 30 is provided with a common wiring 39 in the wiring direction of the signal wiring 36 in order to apply a bias voltage to each pixel 30. By connecting the common wiring 39 to a bias power supply (not shown) outside the sensor substrate 12, a bias voltage is applied to each pixel 30 from the bias power supply.

The power supply unit 108 supplies power to various elements and various circuits such as the controller 100, the driving unit 102, the signal processing unit 104, the image memory 106, and the power supply unit 108. It should be noted that in FIG. 1, in order to avoid complications, wiring for connecting the power supply unit 108 to various elements and various circuits is not shown.

Figure 2A:
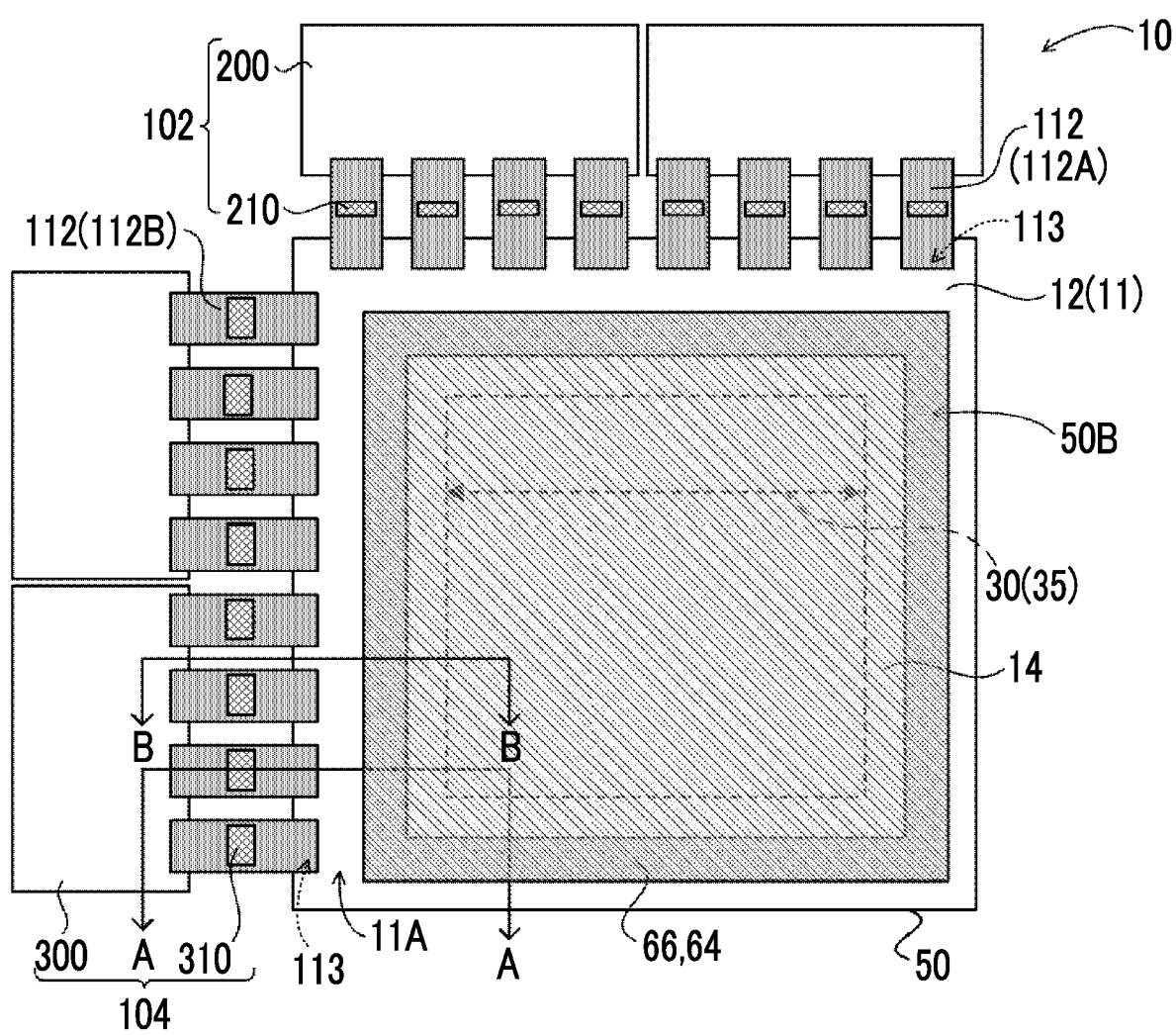
FIG. 2A is a plan view of an example of a radiation detector of the first embodiment as viewed from the first surface side of a base material.
Figure 2B:
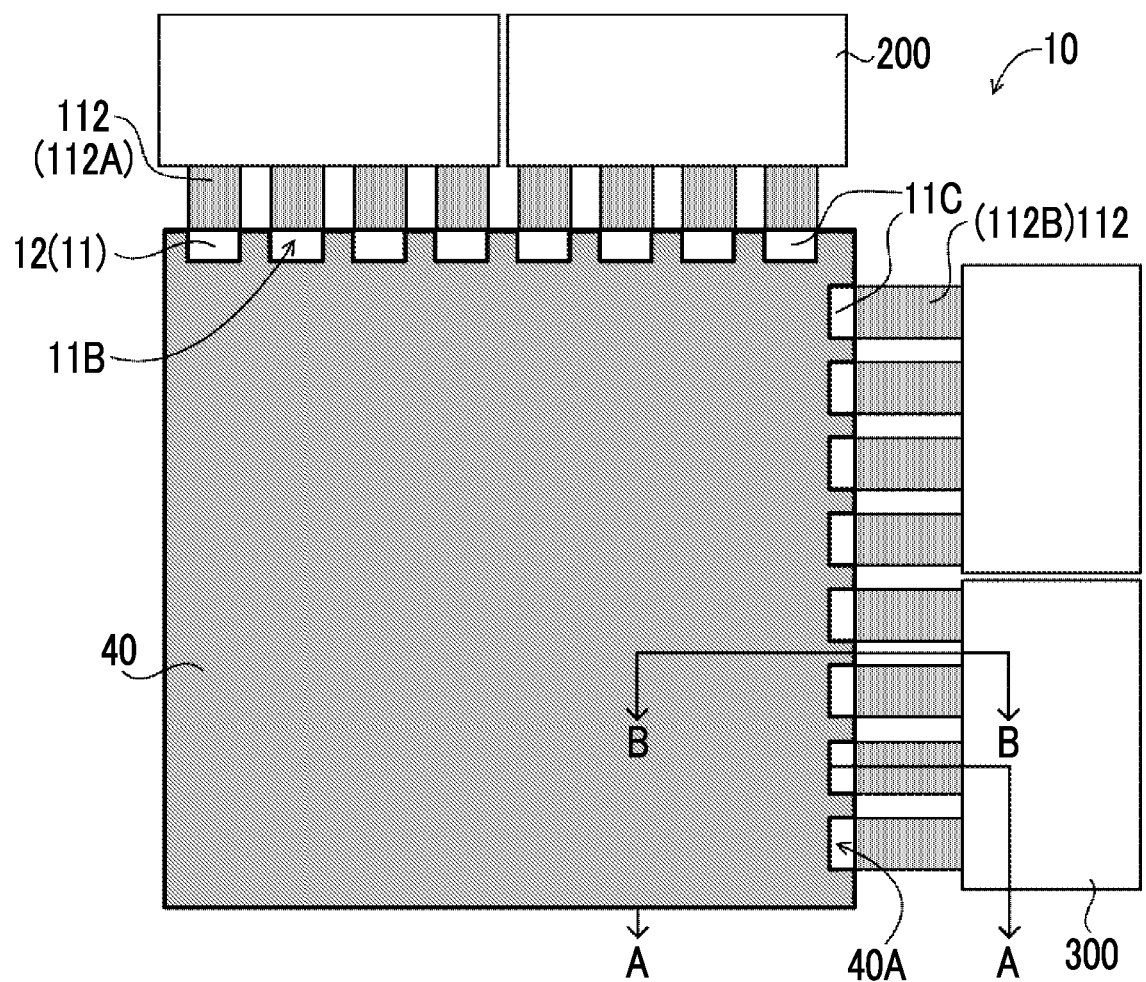
FIG. 2B is a plan view of an example of a radiation detector of the first embodiment as viewed from the second surface side of a base material.
Figure 3A:
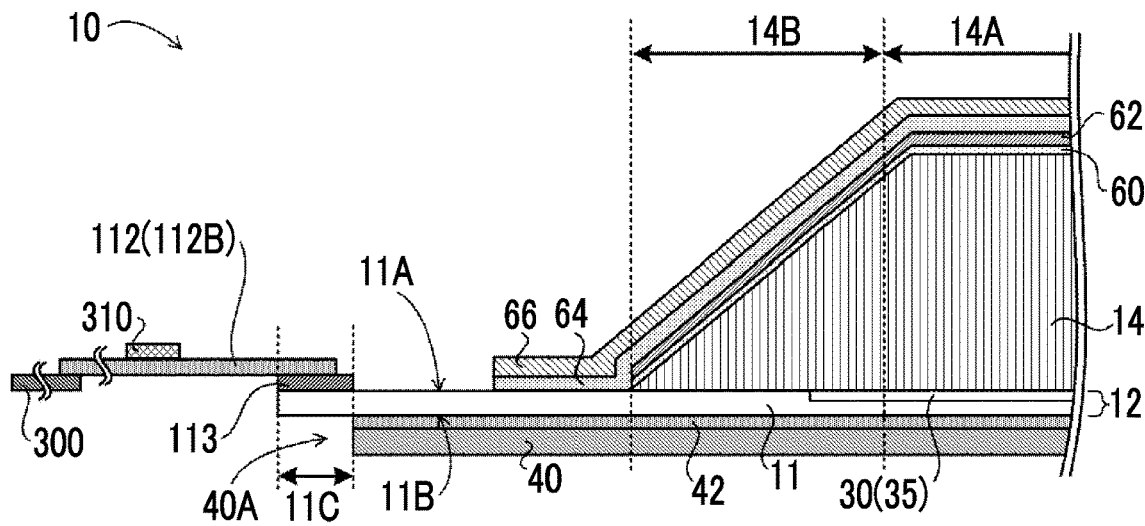
FIG. 3A is a cross-sectional view taken along line A-A of a radiation detector shown in FIG. 2A and FIG. 2B.
Figure 3B:
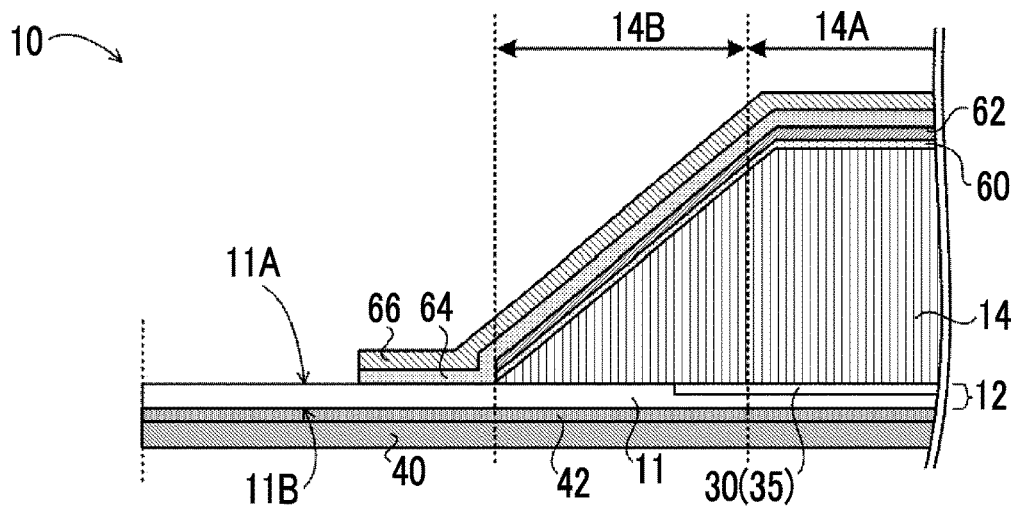
FIG. 3B is a cross-sectional view taken along line B-B of a radiation detector shown in FIG. 2A and FIG. 2B.

Further, the radiation detector 10 will be described in detail. FIG. 2A is an example of a plan view of the radiation detector 10 of the present embodiment as viewed from the first surface 11A side of the base material 11. FIG. 2B is an example of a plan view of the radiation detector 10 of the present embodiment as viewed from the second surface 11B side of the base material 11. In addition, FIG. 3A is an example of a cross-sectional view taken along line A-A of the radiation detector 10 in FIG. 2A and FIG. 2B. FIG. 3B is an example of a cross-sectional view taken along line B-B of the radiation detector 10 in FIG. 2A and FIG. 2B.

The base material 11 has flexibility and is, for example, a resin sheet containing a plastic such as polyImide (PI). The thickness of the base material 11 may be a thickness that the desired flexibility can be obtained depending on the hardness of the material and the size of the sensor substrate 12, that is, the area of the first surface 11A or the second surface 11B. As the example of flexibility, in a case of a single rectangular base material 11, it means that in a state where one side of the base material 11 is fixed, the base material 11 hangs down by 2 mm or more by gravity due to its own weight (fall below the height of the fixed side) at a position 10 cm away from the fixed side. As a specific example in a case where the base material 11 is a resin sheet, a thickness of 5 μm to 125 μm is preferable, and a thickness of 20 μm to 50 μm is more preferable.

It should be noted that the base material 11 has characteristics that can withstand the manufacture of the pixels 30, and in the present embodiment, has characteristics that can withstand the manufacture of amorphous silicon TFTs (a-Si TFT). As the characteristic of the base material 11, the coefficient of thermal expansion (CTE) at 300° C. to 400° C. is preferably about the same as that of an amorphous silicon (Si) wafer (for example, +/−5 ppm/K), and more specifically, it is preferably 20 ppm/K or less. In addition, as for the coefficient of thermal shrinkage of the base material 11, it is preferable that the coefficient of thermal shrinkage at 400° C. is 0.5% or less in a state where the thickness is 25 μm. Further, the elastic modulus of the base material 11 does not have a transition point of general PI in a temperature range between 300° C. and 400° C., and the elastic modulus at 500° C. is preferably 1 GPa or more.

In order to suppress a backscattered radiation by itself, the base material 11 of the present embodiment preferably has a fine particle layer including inorganic fine particles having an average particle size of 0.05 μm or more and 2.5 μm or less and absorbing the backscattered radiation. It should be noted that as the inorganic fine particles, in the case of a resinous base material 11, it is preferable to use an inorganic substance having an atomic number of 30 or less, which is larger than the atoms constituting the organic substance which is the base material 11. Specific examples of such fine particles include $SiO_2$ which is an oxide of Si having an atomic number of 14, MgO which is an oxide of Mg having an atomic number of 12, $Al_2O_3$ which is an oxide of Al having an atomic number of 13, $TiO_2$ which is an oxide of Ti having an atomic number of 22, and the like. Specific examples of the resin sheet having such characteristics include XENOMAX (registered trademark).

It should be noted that the thickness in the present embodiment is measured using a micrometer. The coefficient of thermal expansion is measured according to JIS K7197: 1991. In the measurement, a test piece is cut out from the main surface of the base material 11 by 15 degrees changing the angle, and the coefficient of thermal expansion of each cutout test piece is measured, and the highest value is determined as the coefficient of thermal expansion of the base material 11. In each of the machine direction (MD) and the transverse direction (TD), the coefficient of thermal expansion is measured between −50° C. and 450° C. at 10° C. intervals, and (ppm/° C.) is converted into (ppm/K). The coefficient of thermal expansion is measured using a TMA 4000 S apparatus manufactured by MAC Science, with a sample length of 10 mm, a sample width of 2 mm, an initial load of 34.5 g/mm$^2$, a heating rate of 5° C./min, and an atmosphere of argon.

The base material 11 having desired flexibility is not limited to a resin material such as a sheet made of resin. For example, the base material 11 may be a glass substrate or the like having a relatively thin thickness. As a specific example in a case where the base material 11 is a glass substrate, in general, a size having a side of about 43 cm has flexibility in a case where the thickness is 0.3 mm or less. Therefore, a desired glass substrate may be used as long as the thickness is 0.3 mm or less.

As shown in FIG. 2A, FIG. 3A, and FIG. 3B, the plurality of pixels 30 are provided on the first surface 11A of the base material 11. In the present embodiment, a region in which the pixels 30 are provided on the first surface 11A of the base material 11 is denoted by a pixel region 35.

On the first surface 11A of the base material 11, the conversion layer 14 is provided. The conversion layer 14 of the present embodiment covers the pixel region 35. In the present embodiment, a scintillator containing cesium iodide (CsI) is used as an example of the conversion layer 14. The scintillator preferably contains, for example, CsI: Tl (thallium-Added Cesium iodide) or CsI: Na (cesium iodide to which sodium has been added) whose emission spectrum upon X-ray irradiation ranges from 400 nm to 700 nm. A peak emission wavelength of CsI:Tl in a visible light region is 565 nm.

In a case where the conversion layer 14 is formed by using a vapor phase deposition method, as shown in FIG. 3A and FIG. 3B, the conversion layer 14 is formed with an inclination gradually decreasing in thickness toward its outer edge. Hereinafter, a central region of the conversion layer 14 in which the thickness in a case where the manufacturing error and the measurement error are ignored is considered to be substantially constant is referred to as a central portion 14A. In addition, an outer peripheral region of the conversion layer 14 having a thickness of, for example, 90% or less of the average thickness of the central portion 14A of the conversion layer 14 is referred to as a peripheral edge portion 14B. That is, the conversion layer 14 has an inclined surface inclined with respect to the sensor substrate 12 at the peripheral edge portion 14B. Hereinafter, for convenience of explanation, in the case of "upper" and "lower" in the sensor substrate 12, the conversion layer 14 is used as a reference, and a side of the conversion layer 14 facing the sensor substrate 12 is referred to as "lower" and an opposite side is referred to as "upper". For example, the conversion layer 14 is provided on the sensor substrate 12, and the inclined surface of the peripheral edge portion 14B of the conversion layer 14 is inclined such that the conversion layer 14 gradually expands from the upper side to the lower side.

As shown in FIG. 3A and FIG. 3B, on the conversion layer 14 of the present embodiment, a gluing layer 60, a reflective layer 62, an adhesive layer 64, and a protective layer 66 are provided.

The gluing layer 60 covers the entire surface of the conversion layer 14. The gluing layer 60 has a function of fixing the reflective layer 62 on the conversion layer 14. The gluing layer 60 preferably has light-transmitting property. As the material of the gluing layer 60, for example, an acrylic gluing agent, a hot melt gluing agent, and a silicone adhesive can be used. Examples of the acrylic gluing agent include urethane acrylate, acrylic resin acrylate, and epoxy acrylate. Examples of the hot melt gluing agent include thermoplastic plastics such as EVA (ethylene vinyl acetate copolymer resin), EAA (a copolymer resin of ethylene and acrylic acid), EEA (ethylene-ethyl acrylate copolymer resin), and EMMA (ethylene-methyl methacrylate copolymer). The thickness of the gluing layer 60 is preferably 2 μm or more and 7 μm or less. By setting the thickness of the gluing layer 60 to 2 μm or more, the effect of fixing the reflective layer 62 on the conversion layer 14 can be sufficiently exhibited. In addition, the risk of forming an air layer between the conversion layer 14 and the reflective layer 62 can be suppressed. In a case where the air layer is formed between the conversion layer 14 and the reflective layer 62, light emitted from the conversion layer 14 may cause multiple reflections that repeat reflections between the air layer and the conversion layer 14 and between the air layer and the reflective layer 62. Further, by making the thickness of the gluing layer 60 7 μm or less, it is possible to suppress the lowering of a modulation transfer function (MTF) and a detective quantum efficiency (DQE).

The reflective layer 62 covers the entire surface of the gluing layer 60. The reflective layer 62 has a function of reflecting the light converted by the conversion layer 14. The material of the reflective layer 62 is preferably configured by a metal or a resin material containing a metal oxide. As the material of the reflective layer 62, for example, white polyethylene terephthalate (PET), $TiO_2$, $Al_2O_3$, foamed white PET, specular reflective aluminum, and the like can be used. The white PET is obtained by adding a white pigment such as $TiO_2$ or barium sulfate to PET, and the foamed white PET is white PET having a porous surface. In addition, as the material of the reflective layer 62, a laminated membrane of a resin film and a metal film may be used. As the laminated membrane of the resin film and the metal film, for example, an alpet (registered trademark) sheet in which aluminum is laminated on an insulating sheet (film) such as polyethylene terephthalate by adhering an aluminum foil or the like can be included. The thickness of the reflective layer 62 is preferably 10 μm or more and 40 μm or less. By comprising the reflective layer 62 on the conversion layer 14 in this way, the light converted by the conversion layer 14 can be efficiently guided to the pixels 30 of the sensor substrate 12.

The adhesive layer 64 covers the entire surface of the reflective layer 62. An end portion of the adhesive layer 64 extends to the first surface 11A of the base material 11. That is, the adhesive layer 64 is adhered to the base material 11 of the sensor substrate 12 at the end portion. The adhesive layer 64 has a function of fixing the reflective layer 62 and the protective layer 66 to the conversion layer 14. As the material of the adhesive layer 64, the same material as the material of the gluing layer 60 can be used, but the adhesive force of the adhesive layer 64 is preferably greater than that of the gluing layer 60.

The protective layer 66 is provided in a state where the conversion layer 14 covers the entire and the end portion covers a part of the sensor substrate 12. The protective layer 66 functions as a moisture-proof membrane that prevents water from entering the conversion layer 14. As the material of the protective layer 66, for example, an organic membrane containing an organic material such as PET, poly phenylene sulfide (PPS), oriented poly polypropylene (OPP: biaxially oriented polypropylene film), polyethylene naphthalate (PEN), PI, or parylene (registered trademark) can be used. In addition, as the protective layer 66, the laminated membrane of the resin film and the metal film may be used. As the laminated membrane of the resin film and the metal film, for example, the alpet (registered trademark) sheet can be included.

On the other hand, as shown in FIG. 2A, FIG. 3A, and FIG. 3B, on an outer edge portion of the first surface 11A of the base material 11, a plurality of (16 in FIG. 2A) terminals 113 are provided. An anisotropic conductive film or the like is used as the terminal 113. As shown in FIG. 2A, FIG. 3A, and FIG. 3B, the flexible cable 112 is electrically connected to each of the plurality of terminals 113. Specifically, as shown in FIG. 2A, the flexible cable 112A is thermally compressed to each of a plurality of (8 terminals in FIG. 2A) terminals 113 provided on one side of the base material 11. The flexible cable 112A is a so-called chip on film (COF), and the flexible cable 112A is mounted with a driving integrated circuit (IC) 210. The driving IC 210 is connected to a plurality of signal lines included in the flexible cable 112A. In the present embodiment, in a case where the flexible cable 112A and the flexible cable 112B described later are collectively referred to without distinguishing each other, they are simply referred to as "flexible cable 112".

In the flexible cable 112A, one end electrically connected to the terminal 113 of the sensor substrate 12 and the other end on the opposite side are electrically connected to a driving substrate 200. As an example, in the present embodiment, a plurality of signal lines included in the flexible cable 112A are thermally compressed to the driving substrate 200 to be electrically connected to circuits, elements, and the like (not shown) mounted on the driving substrate 200. It should be noted that the method of electrically connecting the driving substrate 200 and the flexible cable 112A is not limited to the present embodiment, and may be, for example, electrically connected by a connector. Examples of such a connector include a zero insertion force (ZIF) structure connector and a Non-ZIF structure connector.

The driving substrate 200 of the present embodiment is a flexible printed circuit board (PCB) substrate, which is a so-called flexible substrate. In addition, the circuit components (not shown) mounted on the driving substrate 200 are components (hereinafter referred to as "digital components") mainly used for processing digital signals. Digital components tend to have a relatively smaller area (size) than analog components, which will be described later. Specific examples of digital components include digital buffers, bypass capacitors, pull-up/pull-down resistors, damping resistors, electro magnetic compatibility (EMC) countermeasure chip components, and power supply ICs. It should be noted that the driving substrate 200 may not be a flexible substrate, may be a non-flexible rigid substrate, or may be a rigid flexible substrate.

In the present embodiment, the driving substrate 200 and the driving IC 210 mounted on the flexible cable 112A realize the driving unit 102. It should be noted that the driving IC 210 includes a circuit different from the digital components mounted on the driving substrate 200 among various circuits and elements for realizing the driving unit 102.

On the other hand, the flexible cable 112B is electrically connected to each of a plurality of (8 terminals in FIG. 2A) terminals 113 provided on a side where the flexible cable 112A intersects one side of the base material 11 to which the flexible cable is electrically connected. The flexible cable 112B, like the flexible cable 112A, is a so-called COF, and the flexible cable 112B is mounted with a signal processing IC 310. The signal processing IC 310 is connected to a plurality of signal lines (not shown) included in the flexible cable 112B.

The other end of the flexible cable 112B opposite to the one end electrically connected to the terminal 113 of the sensor substrate 12 is electrically connected to a signal processing substrate 300. As an example, in the present embodiment, a plurality of signal lines included in the flexible cable 112B are thermally compressed to the signal processing substrate 300 to be connected to circuits, elements, and the like (not shown) mounted on the signal processing substrate 300. It should be noted that the method of electrically connecting the signal processing substrate 300 and the flexible cable 112B is not limited to the present embodiment, and may be, for example, electrically connected by a connector. Examples of such a connector include the ZIF structure connector and a Non-ZIF structure connector. In addition, the method of electrically connecting the flexible cable 112A to the driving substrate 200 and the method of electrically connecting the flexible cable 112B to the signal processing substrate 300 may be the same or different. For example, the flexible cable 112A and the driving substrate 200 may be electrically connected by being thermally compressed, and the flexible cable 112B and the signal processing substrate 300 may be electrically connected by a connector.

The signal processing substrate 300 of the present embodiment is a flexible PCB substrate, which is a so-called flexible substrate, like the driving substrate 200 described above. The circuit components (not shown) mounted on the signal processing substrate 300 are components (hereinafter referred to as "analog components") mainly used for processing analog signals. Specific examples of the analog components include a charge amplifier, an analog-to-digital converter (ADC), a digital-to-analog converter (DAC), and a power supply ICs. In addition, the circuit components of the present embodiment also include a coil around a power supply source, which has a relatively large component size, and a smoothing large-capacity capacitor. It should be noted that the signal processing substrate 300 may not be a flexible substrate, may be a non-flexible rigid substrate, or may be a rigid flexible substrate.

In the present embodiment, the signal processing substrate 300 and the signal processing IC 310 mounted on the flexible cable 112B realize the signal processing unit 104. It should be noted that the signal processing IC 310 includes a circuit different from the analog components mounted on the signal processing substrate 300 among various circuits and elements for realizing the signal processing unit 104.

In FIG. 2A and FIG. 2B, a plurality of driving substrates 200 and signal processing substrates 300 (two at a time) are provided, but the number of driving substrates 200 and signal processing substrates 300 is not limited to the number shown in FIG. 2A and FIG. 2B. For example, at least one of the driving substrate 200 or the signal processing substrate 300 may be a single substrate.

On the other hand, as shown in FIG. 3A, in the radiation detector 10 of the present embodiment, the flexible cable 112 is thermally compressed to the terminal 113, whereby the flexible cable 112 is electrically connected to the terminal 113. It should be noted that FIG. 3A is a view showing an example of a structure related to the electrical connection between the flexible cable 112B and the radiation detector 10, but a structure related to the electrical connection between the flexible cable 112A and the radiation detector 10 of the present embodiment is also the same as the aspect exemplified in FIG. 3A.

In addition, as shown in FIG. 2B, FIG. 3A, and FIG. 3B, a reinforcing substrate 40 is provided on the second surface 11B of the base material 11 in the sensor substrate 12 of the radiation detector 10 of the present embodiment.

The reinforcing substrate 40 has a function of reinforcing the stiffness of the base material 11. The reinforcing substrate 40 of the present embodiment has higher bending stiffness than the base material 11, and a dimensional change (deformation) with respect to the force applied in the direction perpendicular to the surface facing the conversion layer 14 is smaller than a dimensional change with respect to the force applied in the direction perpendicular to the second surface 11B of the base material 11. Examples of the material of the reinforcing substrate 40 include carbon and plastic. It should be noted that the reinforcing substrate 40 may include a plurality of materials, and may be, for example, a laminate of plastic and carbon.

It should be noted that specifically, the bending stiffness of the reinforcing substrate 40 is preferably 100 times or more of the bending stiffness of the base material 11. In addition, the thickness of the reinforcing substrate 40 of the present embodiment is larger than the thickness of the base material 11. For example, in a case where XENOMAX (registered trademark) is used as the base material 11, the thickness of the reinforcing substrate 40 is preferably about 0.2 mm to 0.25 mm.

Specifically, the reinforcing substrate 40 of the present embodiment preferably uses a material having a bending elastic modulus of 150 MPa or more and 2500 MPa or less. From the viewpoint of suppressing the bending of the base material 11, the reinforcing substrate 40 preferably has higher bending stiffness than the base material 11. It should be noted that the lower the bending elastic modulus, the lower the bending stiffness, and in order to obtain a desired bending stiffness, the thickness of the reinforcing substrate 40 is increased, and thus the thickness of the radiation detector 10 as a whole increases. In consideration of the material of the reinforcing substrate 40 described above, in a case where the bending stiffness exceeding 140,000 Pacm$^4$ is to be obtained, the thickness of the reinforcing substrate 40 tends to be relatively thick. Therefore, in view of the proper stiffness and the thickness of the radiation detector 10 as a whole, the material used for the reinforcing substrate 40 preferably has a bending elastic modulus of 150 MPa or more and 2500 MPa or less. In addition, the bending stiffness of the reinforcing substrate 40 is preferably 540 Pacm$^4$ or more and 140,000 Pacm$^4$ or less.

Further, the coefficient of thermal expansion of the reinforcing substrate 40 of the present embodiment is preferably close to that of the material of the conversion layer 14, and more preferably, a ratio of the coefficient of thermal expansion of the reinforcing substrate 40 to that of the conversion layer 14 (the coefficient of thermal expansion of the reinforcing substrate 40/the coefficient of thermal expansion of the conversion layer 14) is preferably 0.5 to 2. The coefficient of thermal expansion of such a reinforcing substrate 40 is preferably 30 ppm/K to 80 ppm/K. For example, in a case where the conversion layer 14 is made of CsI:Tl as a material, the coefficient of thermal expansion is 50 ppm/K. In this case, materials relatively close to the conversion layer 14 include polyvinyl chloride (PVC) having a coefficient of thermal expansion of 60 ppm/K to 80 ppm/K, acryl having a coefficient of thermal expansion of 70 ppm/K to 80 ppm/K, PET having a coefficient of thermal expansion of 65 ppm/K to 70 ppm/K, polycarbonate (PC) having a coefficient of thermal expansion of 65 ppm/K, and Teflon (registered trademark) having a coefficient of thermal expansion of 45 ppm/K to 70 ppm/K. Further, considering the above-described bending elastic modulus, the material of the reinforcing substrate 40 is more preferably a material including at least one of PET or PC.

From the viewpoint of elasticity, the reinforcing substrate 40 preferably includes a material having a yield point. In the present embodiment, the term "yield point" refers to a phenomenon in which the stress drops abruptly once in a case where the material is pulled, and refers to a point where the strain increases without increasing the stress on a curve representing a relationship between the stress and the strain, and refers to the top of a stress-strain curve in a case where a tensile strength test is performed on the material. Resins having the yield point generally include resins that are hard and tough, and resins that are soft and tough and have medium intensity. Examples of the hard and tough resin include PC and the like. In addition, as the resin having softness and tough viscosity, and medium intensity, for example, polypropylene and the like can be included.

In a case where the reinforcing substrate 40 of the present embodiment is a substrate made of plastic, it is preferably a thermoplastic resin for the reasons described above, and at least one of PC, PET, styrol, acryl, polyacetase, nylon, polypropylene, acrylonitrile butadiene styrene (ABS), engineering plastic and polyphenylene ether is included. It should be noted that the reinforcing substrate 40 is preferably at least one of polypropylene, ABS, engineering plastic, PET, or polyphenylene ether, more preferably at least one of styrene, acryl, polyacetase, or nylon, and more preferably at least one of PC or PET.

Specifically, the reinforcing substrate 40 of the present embodiment is provided in the second surface 11B of the base material 11 in a region excluding at least the facing region 11C facing the terminal 113. Therefore, as shown in FIG. 2B, the reinforcing substrate 40 of the present embodiment is provided with a cutout portion 40A at a position corresponding to the facing region 11C. In the example shown in FIG. 2B, the cutout portion 40A is provided at each position corresponding to the facing region 11C of the second surface 11B facing each of the 16 terminals 113 provided on the first surface 11A.

As described above, in a case where the flexible cable 112 is electrically connected to the terminal 113, heat treatment for thermally compressing the terminal 113 and the flexible cable 112 is performed. By this heat treatment, the heat applied to the terminal 113 is applied to the base material 11, and the heat is propagated to the reinforcing substrate 40. The reinforcing substrate 40 may be deformed by the propagated heat. In a case where the reinforcing substrate 40 is deformed, for example, the reinforcing substrate 40 may be peeled off from the base material 11. In addition, for example, following the deformation of the reinforcing substrate 40, the base material 11 may also deform, and the electrical connection between the flexible cable 112 and the terminal 113 may be cut, or the image quality of the radiographic image obtained by the radiation detector 10 may be affected.

The heat applied to the base material 11 by the heat treatment mainly tends to propagate from the facing region 11C of the second surface 11B to the reinforcing substrate 40. Therefore, in the radiation detector 10 of the present embodiment, as shown in FIG. 2B and FIG. 3A, the facing region 11C is not provided with the reinforcing substrate 40 and the gluing agent 42. Therefore, as shown in FIG. 2B, the side of the reinforcing substrate 40 facing the side where the facing region 11C of the base material 11 are arranged is provided with the cutout portion 40A as described above.

On the other hand, in a region of the second surface 11B excluding the facing region 11C, in which the amount of heat propagated to the reinforcing substrate 40 by the heat treatment is relatively lower than the facing region 11C, the reinforcing substrate 40 and the gluing agent 42 are provided. As described above, since the reinforcing substrate 40 is provided in the region extending to the side of the base material 11, the stiffness of the base material 11 can be appropriately reinforced.

In particular, as shown in FIG. 2A and FIG. 3B, since the reinforcing substrate 40 is provided in a region extending to at least a partial region of the side of the base material 11, in which the terminal 113 is provided, the stiffness of the base material 11 in the vicinity of the terminal 113 can be reinforced.

Therefore, in a case where the flexible cable 112 is electrically connected to the terminal 113, the stiffness in the vicinity of the terminal 113 is reinforced by the reinforcing substrate 40, so that displacement of the flexible cable 112 caused by bending of the flexible base material 11 is less likely to occur.

Figure 4:
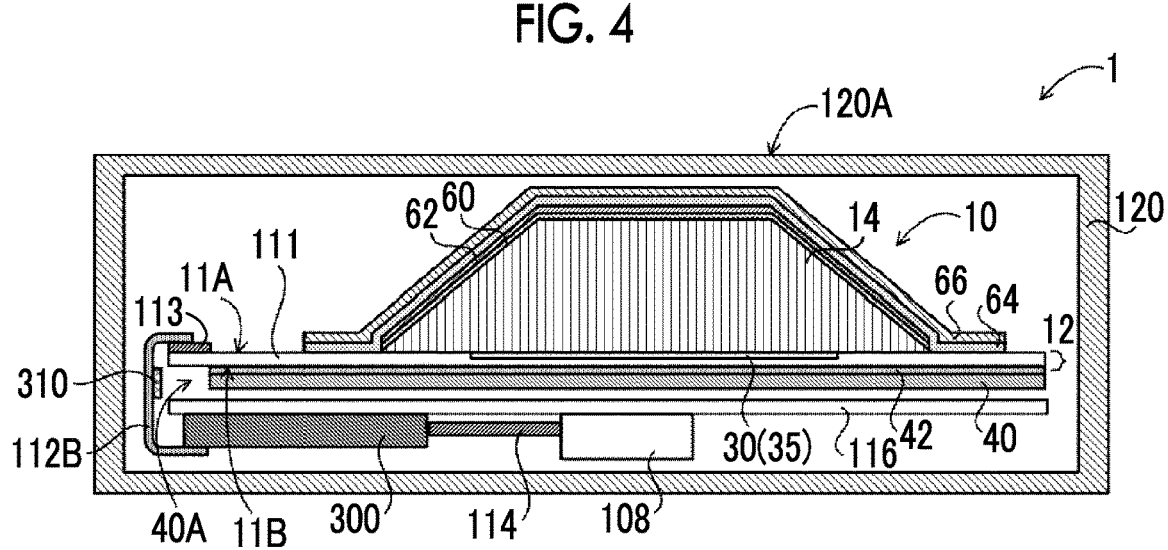
FIG. 4 is a cross-sectional view of an example of a radiography apparatus of the first embodiment.

Further, the radiography apparatus 1 will be described in detail. FIG. 4 is an example of a cross-sectional view of the radiography apparatus 1 of the present embodiment. The radiography apparatus 1 shown in FIG. 4 is a radiography apparatus 1 in which the radiation detector 10 of the present embodiment is applied to a penetration side sampling (PSS) system in which radiation is irradiated from the conversion layer 14 side.

The radiography apparatus 1 using the radiation detector 10 described above is used in a state of being housed in a housing 120, as shown in FIG. 4. As shown in FIG. 4, in the housing 120, circuit units such as the radiation detector 10, the power supply unit 108, and the signal processing substrate 300 are arranged side by side in the incidence direction of radiation. The radiation detector 10 is disposed on the top plate of the housing 120 on the irradiation surface 120A side to which the radiation transmitted through the subject is irradiated, in a state where the first surface 11A side of the base material 11 faces the top plate. More specifically, the conversion layer 14 is arranged in a state where the conversion layer 14 faces the top plate on the irradiation surface 120A side of the housing 120.

As shown in FIG. 4, a middle plate 116 is further provided in the housing 120 on the side where the radiation transmitted through the radiation detector 10 is emitted. Examples of the middle plate 116 include a sheet made of aluminum or copper. The sheet made of copper is less likely to generate secondary radiation due to the incident radiation, and therefore has a function of preventing scattering to the back, that is, to the conversion layer 14 side. It is preferable that the middle plate 116 covers at least the entire surface of the conversion layer 14 on the side where the radiation is emitted, and also covers the entire conversion layer 14. Further, the circuit unit such as the signal processing substrate 300 is fixed to the middle plate 116.

The housing 120 is preferably configured by a material that is lightweight, has a low absorbance of radiation, particularly X-rays, and is high stiffness, and has a sufficiently high elastic modulus. As the material of the housing 120, it is preferable to use a material having a bending elastic modulus of 10,000 MPa or more. As the material of the housing 120, carbon or carbon fiber reinforced plastics (CFRP) having a bending elastic modulus of about 20,000 MPa to 60,000 MPa can be suitably used.

In a case where the radiography apparatus 1 captures a radiographic image, a load from a subject is applied to the irradiation surface 120A of the housing 120. In a case where the stiffness of the housing 120 is insufficient, the sensor substrate 12 may be bent due to the load from the subject, and problems such as damage to the pixel 30 may occur. Since the radiation detector 10 is housed in the housing 120 consisting of a material having a bending elastic modulus of 10,000 MPa or more, the bending of the sensor substrate 12 due to the load from the subject can be suppressed.

The housing 120 may be formed of different materials for the irradiation surface 120A of the housing 120 and other portions. For example, the portion corresponding to the irradiation surface 120A may be formed of a material having a low radiation absorbance, high stiffness, and a sufficiently high elastic modulus as described above, and the other portion may be formed of a material different from the portion corresponding to the irradiation surface 120A, for example, a material having a lower elastic modulus than the portion of the irradiation surface 120A.

The method of manufacturing the radiography apparatus 1 of the present embodiment will be described with reference to FIG. 5A to FIG. 5F. It should be noted that the method for manufacturing the radiography apparatus 1 of the present embodiment includes the method of manufacturing the radiation detector 10 of the present embodiment.

Figure 5A:
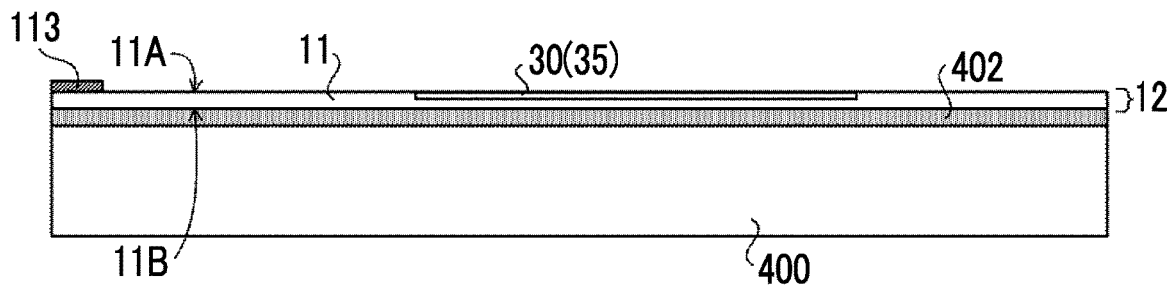
FIG. 5A is a view showing an example of a method of manufacturing a radiography apparatus according to the first embodiment.

As shown in FIG. 5A, in order to form the sensor substrate 12, the base material 11 is provided on a support 400 such as a glass substrate which is thicker than the base material 11 via a peel layer 402. For example, in a case where the base material 11 is formed by a laminating method, a sheet to be the base material 11 is bonded onto the support 400. The second surface 11B of the base material 11 contacts the peel layer 402. It should be noted that the method of forming the base material 11 is not limited to the present embodiment, and may be a form of forming the base material 11 by a coating method, for example.

In addition, the pixels 30 and the terminals 113 are formed on the first surface 11A of the base material 11. The pixels 30 are formed in the pixel region 35 of the first surface 11A via an undercoat layer (not shown) using SiN or the like. Further, a plurality of terminals 113 are formed along each of the two sides of the base material 11.

Figure 5B:
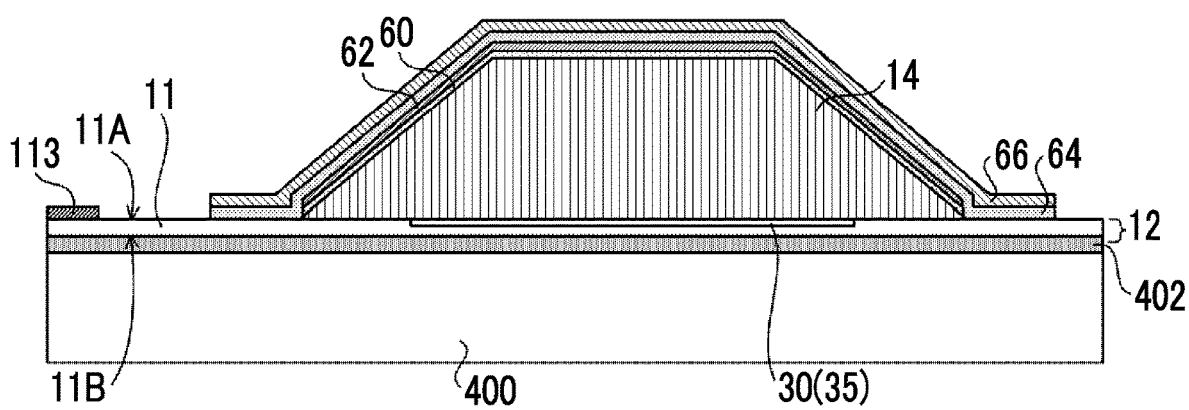
FIG. 5B is a view showing an example of a method of manufacturing a radiography apparatus according to the first embodiment.

Further, as shown in FIG. 5B, the conversion layer 14 is formed on the layer on which the pixels 30 are formed (hereinafter, simply referred to as "pixel 30"). In the present embodiment, the CsI conversion layer 14 is formed as columnar crystals directly on the sensor substrate 12 by the vapor phase deposition method such as a vacuum deposition method, a sputtering method, and a chemical vapor deposition (CVD) method. In this case, the side of the conversion layer 14 in contact with the pixel 30 is a growth direction base point side of the columnar crystals.

In a case where a CsI scintillator is used as the conversion layer 14, the conversion layer 14 can be formed on the sensor substrate 12 by a method different from that of the present embodiment. For example, an aluminum plate or the like plate with CsI vapor-deposited by the vapor phase deposition method may be prepared, and a side of CsI that is not in contact with the aluminum plate and the pixels 30 of the sensor substrate 12 may be bonded together with an gluing sheet or the like to form the conversion layer 14 on the sensor substrate 12. In this case, the entire conversion layer 14 including the aluminum plate is preferably covered with the protective layer and bonded to the pixels 30 of the sensor substrate 12. In this case, the side of the conversion layer 14 in contact with the pixels 30 is the distal end side in the growth direction of the columnar crystals.

In addition, unlike the radiation detector 10 of the present embodiment, GOS ($Gd_2O_2S$:Tb) or the like may be used as the conversion layer 14 instead of CsI. In this case, for example, a sheet in which GOS is dispersed in a binder such as resin is bonded to a support formed of white PET or the like by a gluing layer or the like, and a side on which the support of GOS is not bonded and the pixels 30 of the sensor substrate 12 are bonded to each other by a gluing sheet or the like, so that the conversion layer 14 can be formed on the sensor substrate 12. It should be noted that a conversion efficiency from radiation to visible light is higher a case where CsI is used for the conversion layer 14 than a case where GOS is used.

The reflective layer 62 is provided on the conversion layer 14 formed on the sensor substrate 12 via the gluing layer 60. Further, the protective layer 66 is provided via the adhesive layer 64.

Figure 5C:
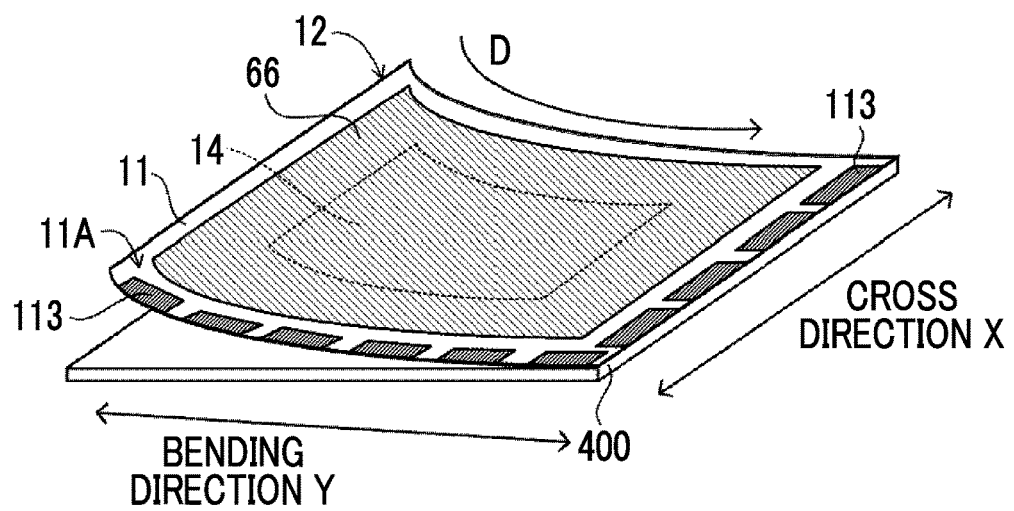
FIG. 5C is a view showing an example of a method of manufacturing a radiography apparatus according to the first embodiment.

After that, as shown in FIG. 5C, the sensor substrate 12 provided with the conversion layer 14 is peeled off from the support 400. Hereinafter, this step is referred to as a peeling step. In the case of mechanical peeling, in the example shown in FIG. 5C, a side of the base material 11 of the sensor substrate 12 opposite to a side provided with the terminal 113 is set as a starting point of peeling, and the sensor substrate 12 is gradually peeled off from the support 400 in the direction of arrow D shown in FIG. 5C from the side serving as the starting point toward the side where the terminal 113 is provided, thereby peeling off the sensor substrate 12 from the support 400.

The side that serves as the starting point of peeling is preferably a side that intersects the longest side in a case where the sensor substrate 12 is viewed in a plan view. In other words, a side along the bending direction Y in which bending occurs due to peeling is preferably the longest side. As an example, in the present embodiment, the starting point of peeling is a side facing a side to which the flexible cable 112B is electrically connected.

Figure 5D:
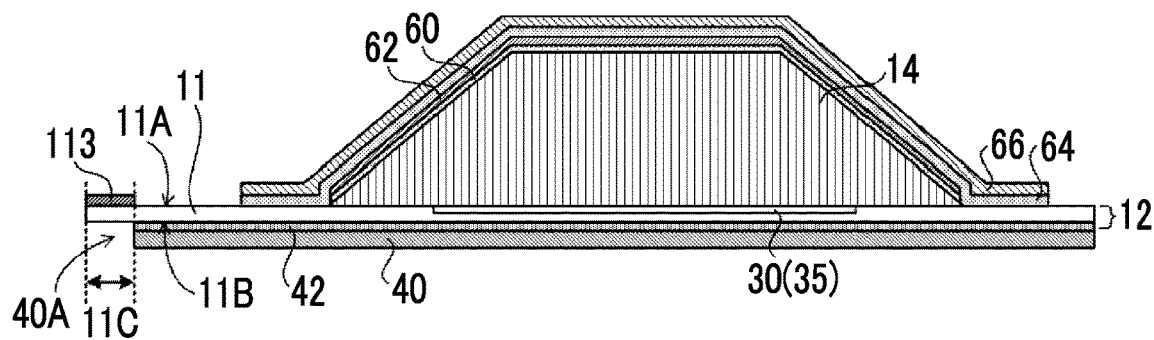
FIG. 5D is a view showing an example of a method of manufacturing a radiography apparatus according to the first embodiment.

Next, as shown in FIG. 5D, the cutout portion 40A of the reinforcing substrate 40 is aligned with the facing region 11C of the second surface 11B of the base material 11, and the reinforcing substrate 40 provided with the gluing agent 42 is bonded to the second surface 11B of the base material 11.

Figure 5E:
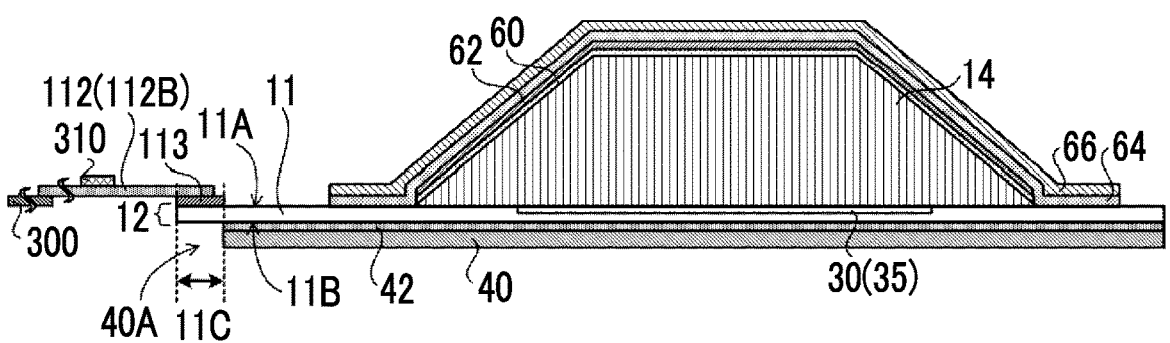
FIG. 5E is a view showing an example of a method of manufacturing a radiography apparatus according to the first embodiment.

Next, as shown in FIG. 5E, the flexible cable 112 is electrically connected to the sensor substrate 12. Specifically, the flexible cable 112 on which the driving IC 210 or the signal processing IC 310 is mounted is thermally compressed to the terminal 113 to electrically connect the terminal 113 and the flexible cable 112. As a result, the flexible cable 112 is electrically connected to the sensor substrate 12.

Figure 5F:
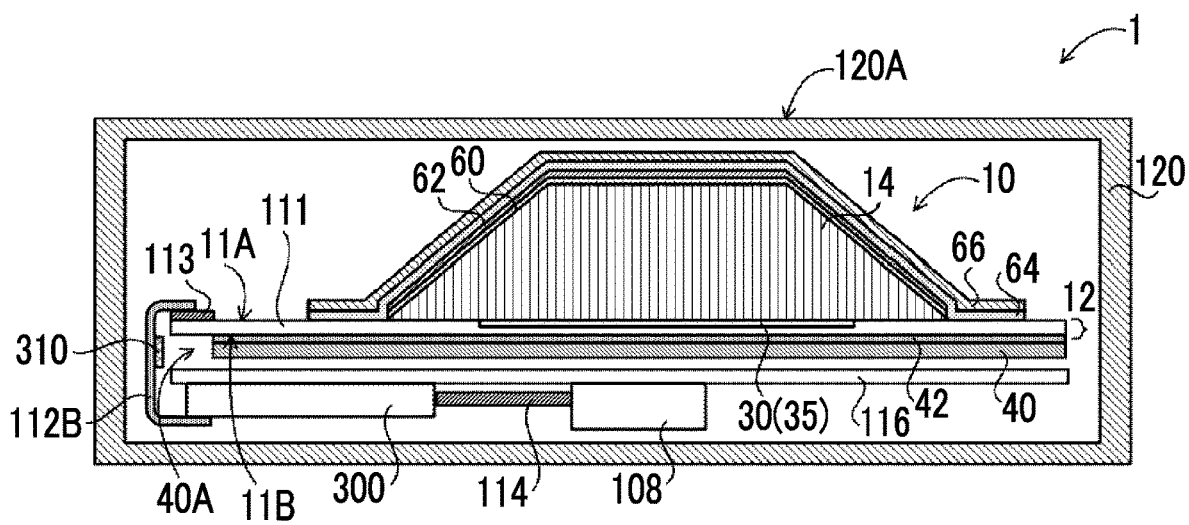
FIG. 5F is a view showing an example of a method of manufacturing a radiography apparatus according to the first embodiment.

Further, as shown in FIG. 5F, the radiation detector 10, the circuit unit, and the like are housed in the housing 120. Specifically, the radiation detector 10 is housed in the housing 120 in a state of the upper side of the conversion layer 14 facing the irradiation surface 120A. In this way, the radiography apparatus 1 of the present embodiment is manufactured.

Second Embodiment

In the present embodiment, another embodiment of the reinforcing substrate 40 will be described. It should be noted that the detailed description of the radiography apparatus 1 and the radiation detector 10 in the present embodiment will be omitted for the same configuration as that in the first embodiment.

Figure 6:
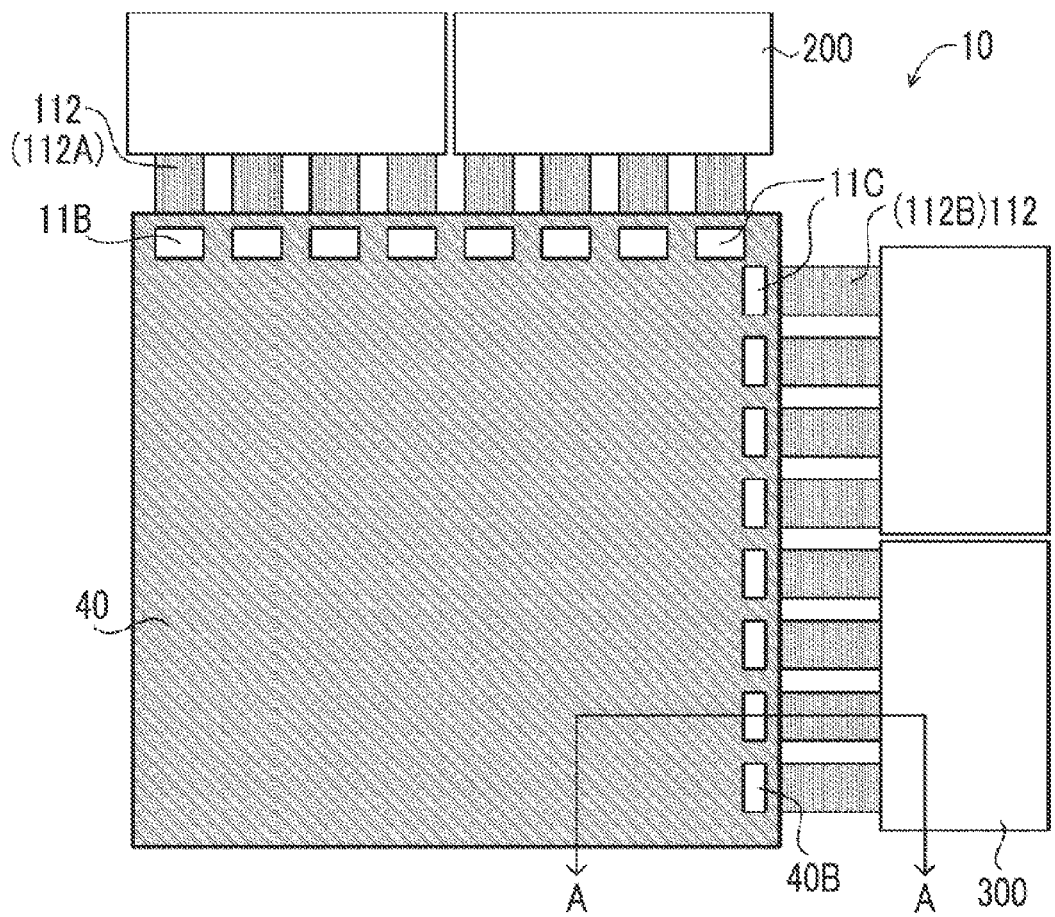
FIG. 6 is a plan view of an example of a radiation detector having a different shape of a reinforcing substrate according to the second embodiment as viewed from the second surface side of the base material.

First, an example of the reinforcing substrate 40 having a shape different from that of the reinforcing substrate 40 of the first embodiment (refer to FIG. 2B and FIG. 3A) will be described. FIG. 6 is an example of a plan view of the radiation detector 10 of the present embodiment as viewed from the second surface 11B side of the base material 11. In addition, FIG. 7 is an example of a cross-sectional view taken along line A-A of the radiation detector 10 in FIG. 6.

Figure 7:
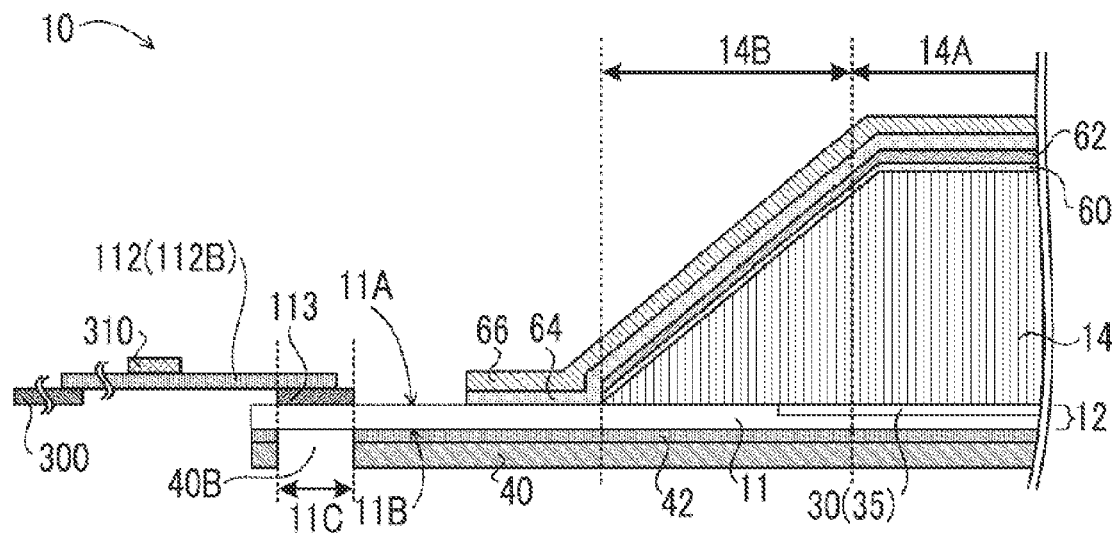
FIG. 7 is a cross-sectional view taken along line A-A of a radiation detector shown in FIG. 6.

As shown in FIG. 7, in the radiation detector 10 of the present embodiment and the radiation detector 10 of the first embodiment, a position where the terminal 113 is provided on the first surface 11A of the base material 11 of the sensor substrate 12 is different. In the radiation detector 10 of the first embodiment, the terminal 113 is provided at a position extending to the side of the base material 11 (refer to FIG. 3A). On the other hand, as shown in FIG. 7, in the radiation detector 10 of the present embodiment, the terminal 113 is provided at a position inside from the side of the base material 11. Therefore, a position of the facing region 11C of the base material 11 in the radiation detector 10 of the present embodiment is also different from a position of the facing region 11C of the base material 11 (refer to FIG. 2B and FIG. 3A) in the radiation detector 10 of the first embodiment.

As described above, the reinforcing substrate 40 is not provided in the region including the facing region 11C on the second surface 11B of the base material 11. Therefore, as shown in FIG. 6 and FIG. 7, the reinforcing substrate 40 of the present embodiment is provided with a gap portion 40B at a position corresponding to the facing region 11C, and the size (area) of the reinforcing substrate 40 is equal to or larger than that of the base material 11. In the radiation detector 10, the reinforcing substrate 40 provided with the gap portion 40B is provided on the second surface 11B of the base material 11.

Therefore, in the radiation detector 10 shown in FIG. 6 and FIG. 7, since the reinforcing substrate 40 is provided in the region extending to all sides of the base material 11, the stiffness of the base material 11 in the vicinity of the terminal 113 and the outer edge can be appropriately reinforced.

Figure 8:
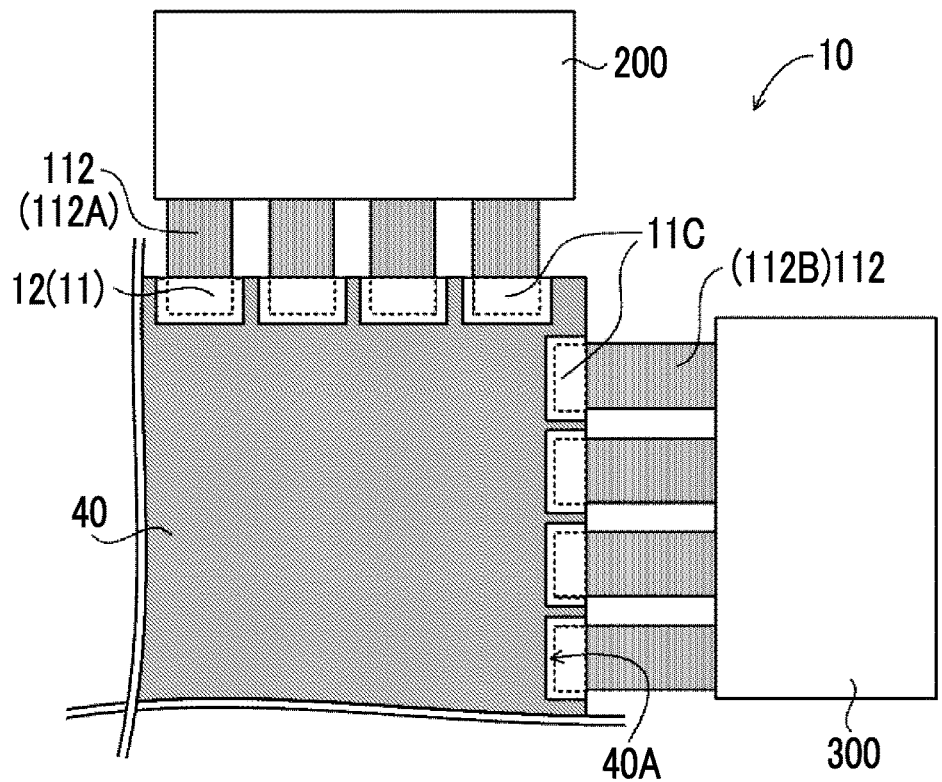
FIG. 8 is a plan view of an example of a radiation detector having a different region in which the reinforcing substrate of the second embodiment is provided, as viewed from the second surface side of the base material.

Next, a description will be given of an example of the reinforcing substrate 40 in a case where a region on the second surface 11B of the base material 11 where the reinforcing substrate 40 is provided is different from the radiation detector 10 (refer to FIG. 2B) of the first embodiment. FIG. 8 is an example of a plan view of the radiation detector 10 of the present embodiment as viewed from the second surface 11B side of the base material 11. As shown in FIG. 8, the reinforcing substrate 40 of the present embodiment is provided on the second surface 11B of the base material 11 except a region including the facing region 11C and larger than the facing region 11C.

As described above, the heat applied to the base material 11 may propagate to the reinforcing substrate 40 by heat treatment performed in a case where the flexible cable 112 is electrically connected to the terminal 113. For example, in a case where a large amount of heat has propagated to the reinforcing substrate 40, a relatively high amount of heat may propagate to a wider range than the facing region 11C on the second surface 11B of the base material 11.

Therefore, in the radiation detector 10 shown in FIG. 8, the reinforcing substrate 40 is provided in a region excluding at least a region where the heat that causes the deformation amount of the reinforcing substrate 40 to exceed a predetermined amount is applied to the base material 11 in the heat treatment performed in a case where the reinforcing substrate includes the facing region 11C and the terminal 113 is electrically connected to the flexible cable 112. In other words, in the radiation detector 10 of the present embodiment, the region of the second surface 11B of the base material 11, where the deformation amount of the reinforcing substrate 40 is subjected to heat exceeding an allowable range in the radiation detector 10, is not provided with the reinforcing substrate 40.

Accordingly, in the radiation detector 10 shown in FIG. 8, even in a case where a relatively high amount of heat is applied to the base material 11 in the heat treatment performed in a case where the flexible cable 112 is electrically connected, the deformation of the reinforcing substrate 40 can be suppressed.

Figure 9:
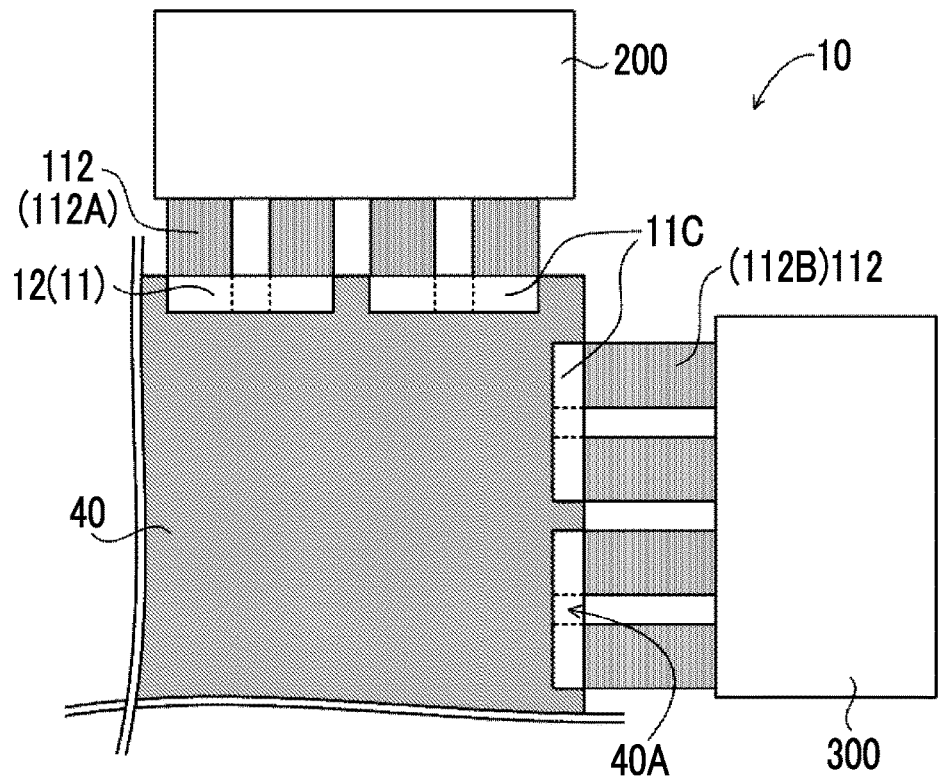
FIG. 9 is a plan view of another example of a radiation detector having a different region in which the reinforcing substrate of the second embodiment is provided, as viewed from the second surface side of the base material.

Next, a description will be given of another example of the reinforcing substrate 40 in a case where a region on the second surface 11B of the base material 11 where the reinforcing substrate 40 is provided is different from the radiation detector 10 (refer to FIG. 2B) of the first embodiment. FIG. 9 is an example of a plan view of the radiation detector 10 of the present embodiment as viewed from the second surface 11B side of the base material 11. As shown in FIG. 9, the reinforcing substrate 40 of the present embodiment is provided on the second surface 11B of the base material 11 except a region including two facing regions 11C.

As shown in FIG. 9, a plurality of facing regions 11C may be formed as a set, and the reinforcing substrate 40 may not be provided in a region corresponding to each set. In this case, in the radiation detector 10, the reinforcing substrate 40 is also not provided in the region between the facing regions 11C included in each set.

For example, in a case where the plurality of terminals 113 are provided on the first surface 11A of the base material 11 at a narrow interval, the base material 11 in the region between the facing region 11C and the facing region 11C may also be heated. In such a case, by reducing the frequency of providing the reinforcing substrate 40 in the region between the facing region 11C and the facing region 11C on the second surface 11B of the base material 11, the deformation of the reinforcing substrate 40 can be suppressed.

It should be noted that in a case where the reinforcing substrate 40 is not provided in a region including all the facing regions 11C with respect to one side of the base material 11 provided with the terminal 113, the stiffness of the outer edge of the base material 11 may be reduced. On the other hand, as shown in the example shown in FIG. 9, in one side of the base material 11 provided with the terminal 113, the reinforcing substrate 40 is provided in one of the regions corresponding between the facing regions 11C, so that it is possible to suppress a reduction in stiffness at the outer edge of the base material 11.

Third Embodiment

In the present embodiment, the method of manufacturing the radiography apparatus 1 will be described with respect to an embodiment different from the first embodiment. It should be noted that the detailed description of the radiography apparatus 1 and the radiation detector 10 in the present embodiment will be omitted for the same configuration as that in the first embodiment.

The method of manufacturing the radiography apparatus 1 of the present embodiment will be described with reference to FIG. 10A to FIG. 10C.

In the method of manufacturing the radiography apparatus 1 of the present embodiment, the steps up to the peeling step, that is, the steps described with reference to each of FIG. 5A to FIG. 5C in the first embodiment are the same, and therefore the description thereof is omitted.

Figure 10A:
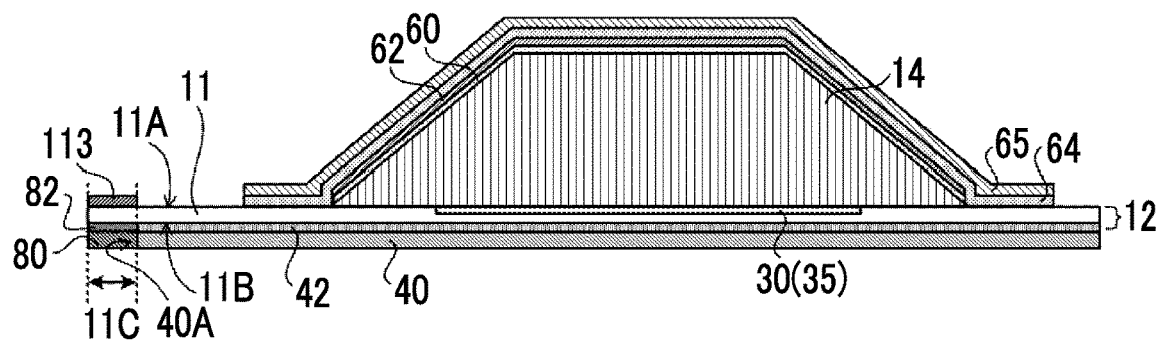
FIG. 10A is a view showing an example of a method of manufacturing a radiography apparatus according to the third embodiment.

In the present embodiment, after the sensor substrate 12 is peeled off from the support 400, as shown in FIG. 10A, the cutout portion 40A of the reinforcing substrate 40 is aligned with the facing region 11C of the second surface 11B of the base material 11, and the reinforcing substrate 40 provided with the gluing agent 42 is bonded to the second surface 11B of the base material 11.

In addition, as shown in FIG. 10A, the replenishing member 80 provided with the gluing agent 82 is bonded to the facing region 11C of the second surface 11B of the base material 11. In other words, the replenishing member 80 is provided on the second surface 11B of the base material 11 in a state where the cutout portion 40A of the reinforcing substrate 40 is filled.

In the region in which the replenishing member 80 is provided, as described above, heat treatment performed in a case where the flexible cable 112 is electrically connected to the terminal 113 causes the heat applied to the base material 11 in the facing region 11C of the second surface 11B of the base material 11 to propagate. Therefore, the heat applied to the base material 11 propagates to the replenishing member 80.

For the replenishing member 80, at least one of a material having a deformation amount for heat smaller than at least the reinforcing substrate 40 or a material having a thermal conductivity higher than at least the reinforcing substrate 40 is used. In a case where the deformation amount of the replenishing member 80 for heat is small, in other words, in a case where the coefficient of thermal expansion of the replenishing member 80 is small, the deformation amount of the replenishing member 80 and the reinforcing substrate 40 caused by the heat applied to the base material 11 in the heat treatment can be reduced. Further, in a case where the thermal conductivity of the replenishing member 80 is high, the heat propagated from the base material 11 to the replenishing member 80 in the heat treatment does not remain and is easily dispersed, so that the deformation amount of the replenishing member 80 and the reinforcing substrate 40 due to the heat can be reduced.

From the viewpoint of a material having a low coefficient of thermal expansion, for example, plastics such as poly ether sulfone (PES) and PPS can be used as the material of the replenishing member 80. In addition, as the material of the replenishing member 80, for example, metals such as aluminum and copper can be used from the viewpoint of thermal conductivity.

It should be noted that the thickness of the replenishing member 80 is preferably the same as the thickness of the reinforcing substrate 40. In other words, it is preferable that a surface of the reinforcing substrate 40 provided on the second surface 11B of the base material 11 opposite to the base material 11 is flush with a surface of the replenishing member 80 opposite to the base material 11.

It should be noted that either the step of providing the reinforcing substrate 40 on the second surface 11B of the base material 11 or the step of providing the replenishing member 80 may be performed first or at the same time.

Figure 10B:
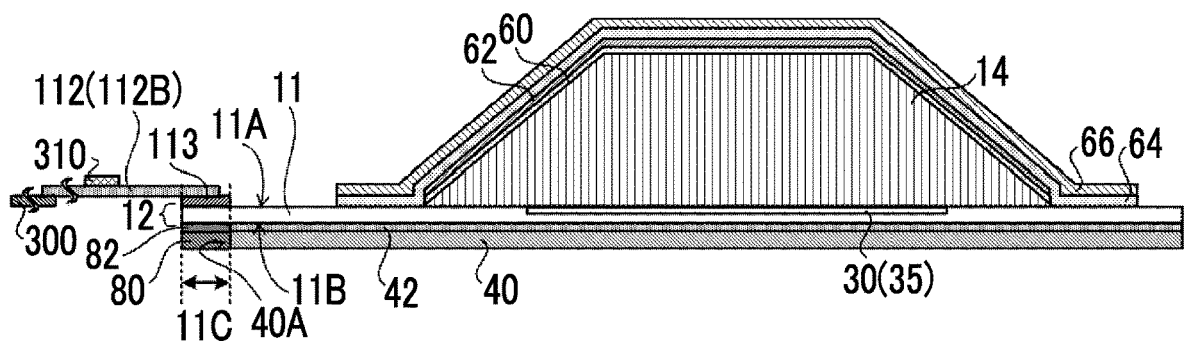
FIG. 10B is a view showing an example of a method of manufacturing a radiography apparatus according to the third embodiment.

Next, as shown in FIG. 10B, the flexible cable 112 is electrically connected to the sensor substrate 12 in the same manner as in the step described with reference to FIG. 5E.

In order to electrically connect the flexible cable 112 to the sensor substrate 12, in a case where the flexible cable 112 is thermally compressed to the terminal 113, the sensor substrate 12 is fixed to a stage of the thermocompression apparatus with the reinforcing substrate 40 and the replenishing member 80 side facing down. Here, as described above, in a case where the heights of the reinforcing substrate 40 and the replenishing member 80 are the same, the sensor substrate 12 can be more stably fixed to the stage. In addition, since the first surface 11A of the base material 11 is in a flat state, it is easy to connect the flexible cable 112 to the terminal 113.

Figure 10C:
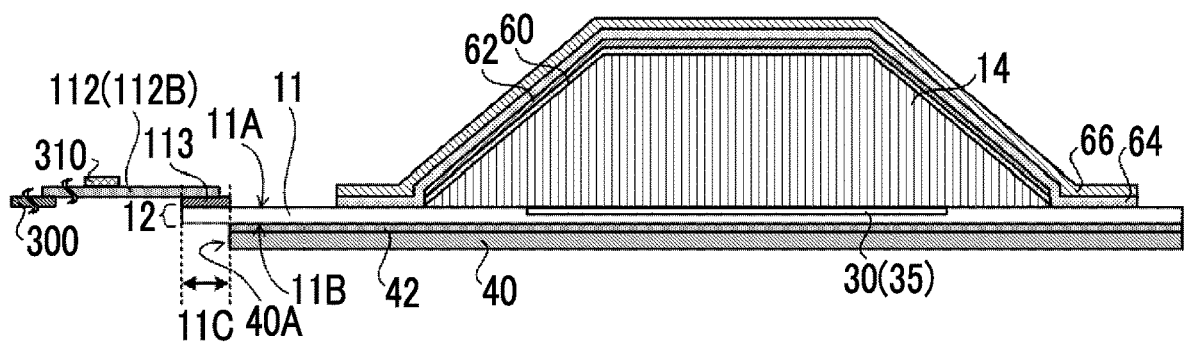
FIG. 10C is a view showing an example of a method of manufacturing a radiography apparatus according to the third embodiment.

Next, as shown in FIG. 10C, the replenishing member 80 is removed from the base material 11 of the sensor substrate 12. From the viewpoint of recycling, it is preferable that the replenishing member 80 removed in this step can be used as the replenishing member 80 in a case where the radiography apparatus 1 is manufactured next time. In a case where it can be recycled in this way, a relatively expensive material can be used as the material of the replenishing member 80.

After the step shown in FIG. 10C, a step of housing the radiation detector 10, the circuit unit, and the like in the housing 120, that is, a step described with reference to FIG. 5F in the first embodiment, is performed to manufacture the radiography apparatus 1 of the present embodiment.

As described above, in the method of manufacturing the radiography apparatus 1 (the radiation detector 10) of the present embodiment, in the second surface 11B of the base material 11, after the replenishing member 80 is provided in the region in which the reinforcing substrate 40 is not provided, the step of electrically connecting the flexible cable 112 to the terminal 113 is performed. Accordingly, it is possible to easily connect the flexible cable 112 to the terminal 113.

It should be noted that the configuration and manufacturing method of the radiography apparatus 1 and the radiation detector 10 are not limited to the above-described aspect. For example, the form shown in the following Modification Examples 1 to 5 may be used. In addition, each of the above-described form and the Modification Example 1 to the Modification Example 5 may be appropriately combined, and the aspect is not limited to the Modification Example 1 to the Modification Example 5.

Modification Example 1

In the present modification example, with reference to FIG. 11A to FIG. 11E, an example of the radiation detector 10 in a case where a reinforcing member 90 for reinforcing the stiffness of the base material 11 is provided on the first surface 11A side of the base material 11 of the sensor substrate 12 will be described. Each of FIG. 11A to FIG. 11E shows an example of a cross-sectional view of the radiation detector 10 of the present modification example corresponding to cross-sectional view taken along line A-A of the radiation detector 10 shown in FIG. 3A.

Figure 11A:
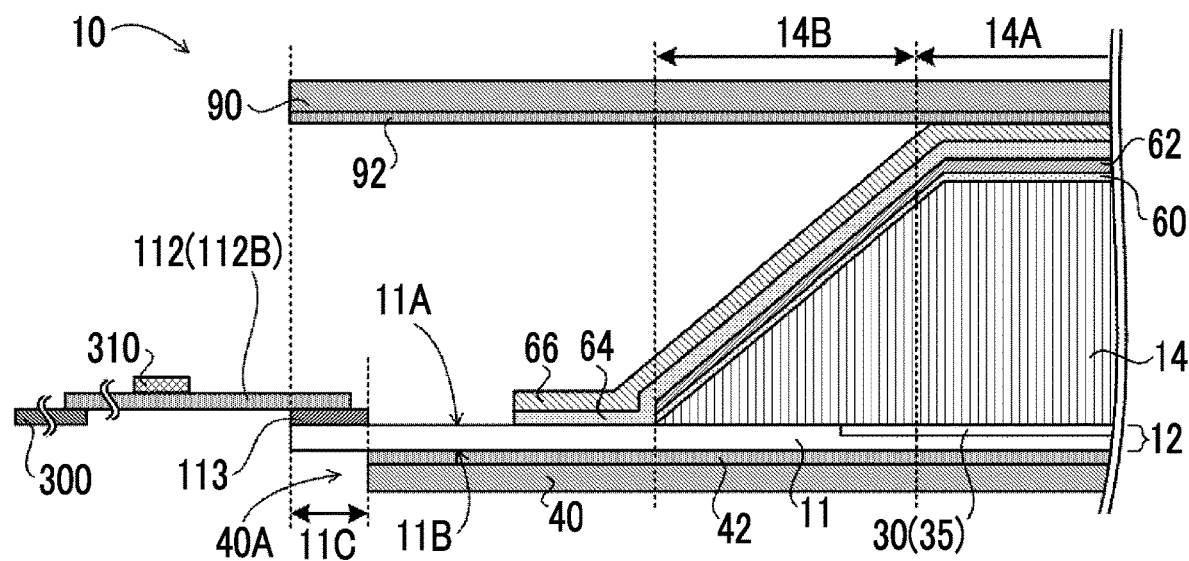
FIG. 11A is a cross-sectional view taken along line A-A of an example of a radiation detector of the Modification Example 1.

As shown in FIG. 11A, the gluing agent 92 and the reinforcing member 90 are provided on the conversion layer 14 provided on the first surface 11A of the base material 11.

The reinforcing member 90 has higher bending stiffness than the base material 11, and a dimensional change (deformation) with respect to the force applied in the direction perpendicular to the surface facing the conversion layer 14 is smaller than the dimensional change with respect to the force applied in the direction perpendicular to the first surface 11A of the base material 11. In addition, the thickness of the reinforcing member 90 of the present modification example is thicker than the thickness of the base material 11.

The preferable characteristics of the reinforcing member 90 are the same characteristics as those of the reinforcing substrate 40 described above. For the reinforcing member 90 of the present modification example, it is preferable to use a material having a bending elastic modulus of 150 MPa or more and 2,500 MPa or less. From the viewpoint of suppressing the bending of the base material 11, the reinforcing member 90 preferably has higher bending stiffness than the base material 11. It should be noted that the lower the bending elastic modulus, the lower the bending stiffness, and in order to obtain a desired bending stiffness, the thickness of the reinforcing member 90 is increased, and thus the thickness of the radiation detector 10 as a whole increases. In consideration of the material of the reinforcing member 90 described above, in a case where the bending stiffness exceeding 140,000 Pacm$^4$ is to be obtained, the thickness of the reinforcing member 90 tends to be relatively thick. Therefore, in view of the proper stiffness and the thickness of the radiation detector 10 as a whole, the material used for the reinforcing member 90 preferably has a bending elastic modulus of 150 MPa or more and 2500 MPa or less. In addition, the bending stiffness of the reinforcing member 90 is preferably 540 Pacm4 or more and 140,000 Pacm$^4$ or less.

Further, the coefficient of thermal expansion of the reinforcing member 90 is preferably close to that of the material of the conversion layer 14, and more preferably, a ratio of the coefficient of thermal expansion of the conversion layer 14 to that of the reinforcing member 90 (the coefficient of thermal expansion of the reinforcing member 90/the coefficient of thermal expansion of the conversion layer 14) is preferably 0.5 to 2. The coefficient of thermal expansion of such a reinforcing member 90 is preferably 30 ppm/K to 80 ppm/K. For example, in a case where the conversion layer 14 is made of CsI:Tl as a material, the coefficient of thermal expansion is 50 ppm/K. In this case, examples of the material relatively close to the conversion layer 14 include PVC, acryl, PET, PC, Teflon (registered trademark) and the like. Further, considering the above-described bending elastic modulus, the material of the reinforcing member 90 is more preferably a material including at least one of PET or PC. In addition, from the viewpoint of elasticity, the reinforcing member 90 preferably includes a material having a yield point.

The reinforcing member 90 of the present modification example is a substrate made of plastic. The plastic material of the reinforcing member 90 is preferably a thermoplastic resin for the reasons described above, and includes at least one of PC, PET, styrol, acryl, polyacetase, nylon, polypropylene, ABS, engineering plastic, or polyphenylene ether. It should be noted that the reinforcing member 90 is, among the materials, preferably at least one of polypropylene, ABS, engineering plastic, PET, or polyphenylene ether, more preferably at least one of styrol, acryl, polyacetase, or nylon, and more preferably at least one of PC or PET.

The specific characteristics and materials of the reinforcing member 90 and the reinforcing substrate 40 may be the same or different.

The entire surface of the reinforcing member 90 facing the sensor substrate 12 is provided with the gluing agent 92, and the gluing agent 92 is provided on the conversion layer 14, more specifically, on the reflective layer 62 covering the conversion layer 14.

The step of providing the reinforcing member 90 on the conversion layer 14 may be performed after the peeling step (refer to FIG. 5C), but is preferably performed before the peeling step. In a case where the sensor substrate 12 provided with the conversion layer 14 is peeled off from the support 400, the base material 11 bends. In a case where the base material 11 bends, there is a concern that the conversion layer 14, particularly the end portion of the conversion layer 14, may peel off from the base material 11. On the other hand, in a case where the sensor substrate 12 provided with the reinforcing member 90 on the conversion layer 14 is peeled off from the support 400, since the bending stiffness of the base material 11 is reinforced, the peeling of the conversion layer 14 from the base material 11 caused by the bending of the base material 11 can be suppressed.

Figure 11B:
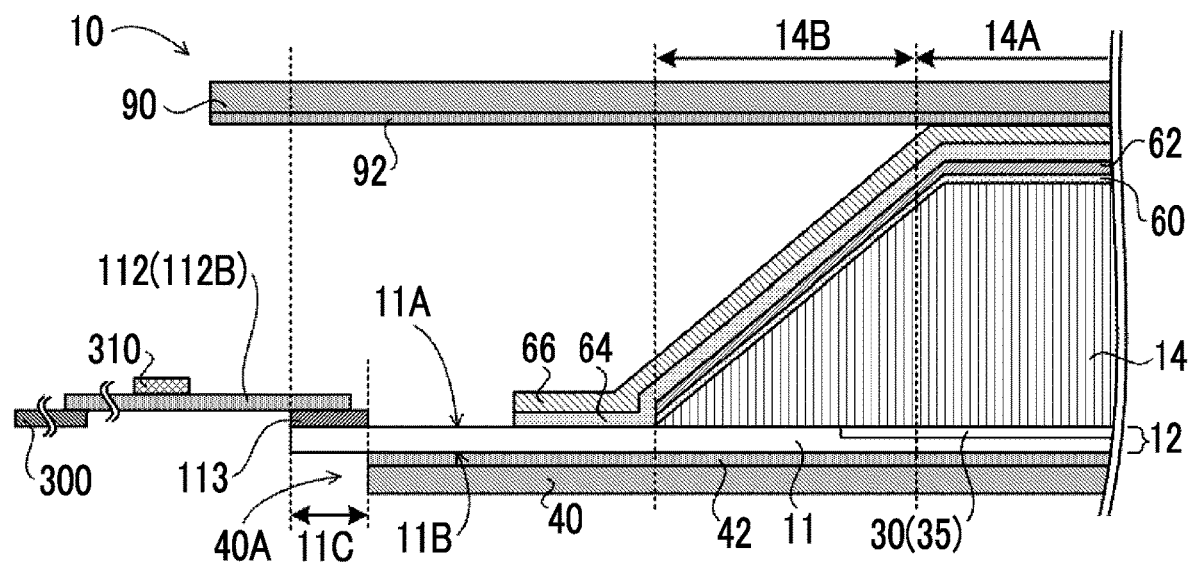
FIG. 11B is a cross-sectional view taken along line A-A of another example of a radiation detector of the Modification Example 1.

In the radiation detector 10 shown in FIG. 11A, an example is shown in which the reinforcing member 90 has the same size (area) as the base material 11, and the end portion of the reinforcing member 90 and the end portion of the base material 11 have the same position. However, the size and the position of the end portion of the reinforcing member 90 are not limited to this example. For example, as shown in FIG. 11B, the reinforcing member 90 may be larger than the base material 11. It should be noted that the specific size of the reinforcing member 90 can be determined according to the internal size of the housing 120 for housing the radiation detector 10. Further, as shown in FIG. 11B, the end portion of the reinforcing member 90 is located outside the end portion of the base material 11, that is, the sensor substrate 12.

By making the size of the reinforcing member 90 larger than the base material 11 in this way, for example, in a case where the radiography apparatus 1 is dropped, an impact is applied to the housing 120, and a side surface (a surface that intersects the irradiation surface 120A) of the housing 120 is recessed, the reinforcing member 90 interferes with the side surface of the housing 120. On the other hand, since the sensor substrate 12 is smaller than the reinforcing member 90, it is less likely to interfere with the side surface of the housing 120. Accordingly, according to the radiation detector 10 shown in FIG. 11B, it is possible to suppress the influence of the impact applied to the radiography apparatus 1 on the sensor substrate 12.

From the viewpoint of suppressing the influence of the impact applied to the radiography apparatus 1 by the reinforcing member 90 on the sensor substrate 12, as shown in FIG. 11B, at least a part of the end portion of the reinforcing member 90 may protrude outward from the end portion of the base material 11. For example, even in a case where the size of the reinforcing member 90 is smaller than that of the base material 11, the end portion of the reinforcing member 90 more protruding outward than the end portion of the base material 11 is interfered with the side surface of the housing 120, so that the influence of the impact on the sensor substrate 12 can be suppressed.

Figure 11C:
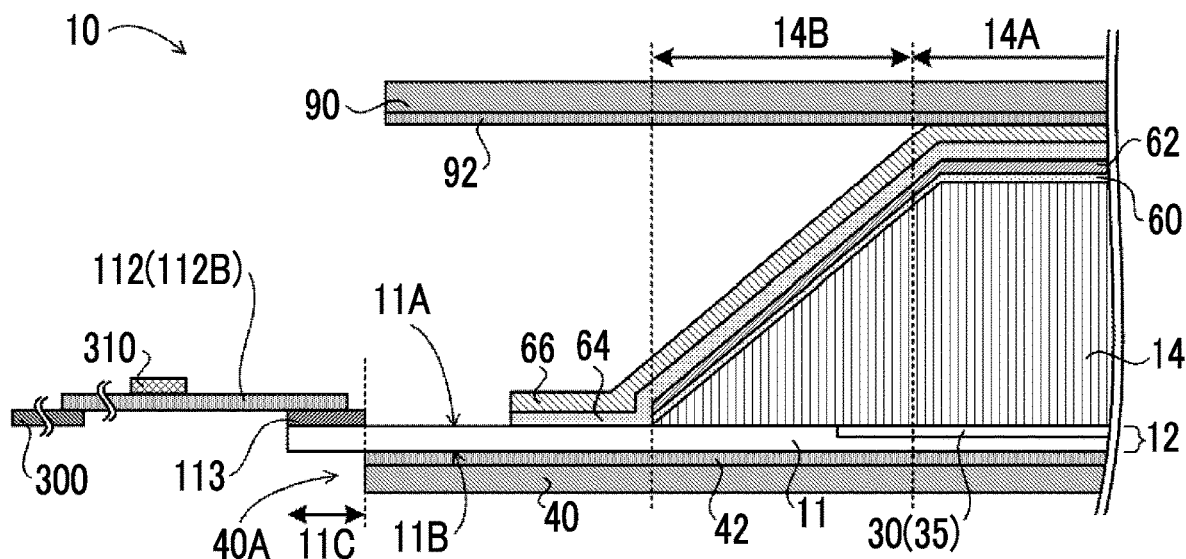
FIG. 11C is a cross-sectional view taken along line A-A of another example of a radiation detector of the Modification Example 1.
Figure 11D:
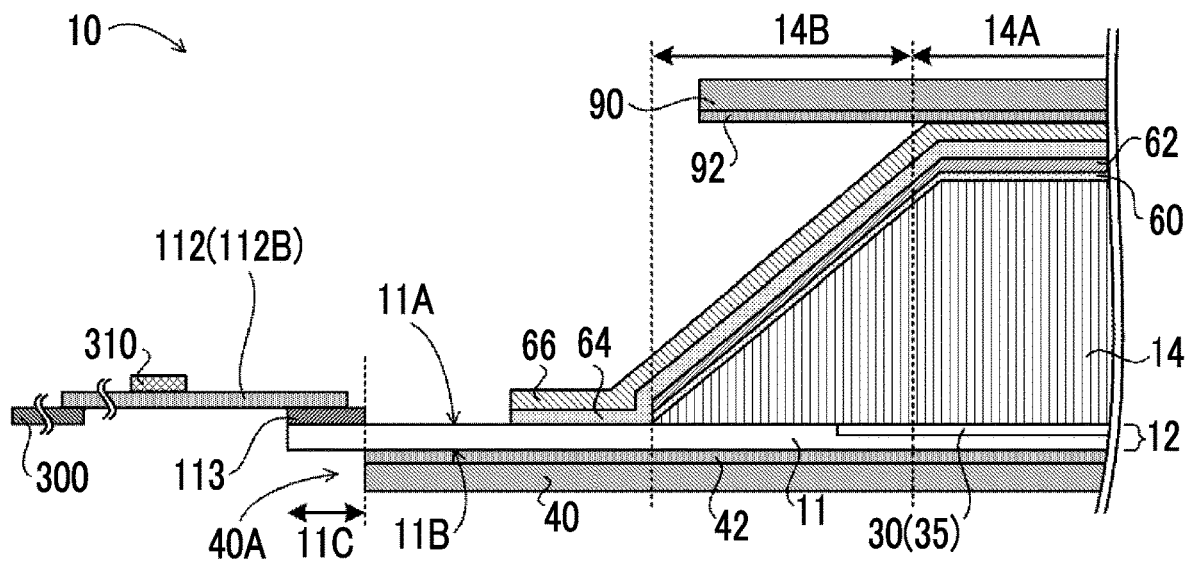
FIG. 11D is a cross-sectional view taken along line A-A of another example of a radiation detector of the Modification Example 1.

In addition, for example, as shown in FIG. 11C and FIG. 11D, the reinforcing member 90 may be smaller than the base material 11. In the example shown in FIG. 11C, the reinforcing member 90 is not provided at the position facing the terminal 113. That is, the area of the reinforcing member 90 in the radiation detector 10 of the present modification example is smaller than a value obtained by subtracting the area of the region in which the terminal 113 is provided from the area of the base material 11. On the other hand, in the example shown in FIG. 11D, the end portion of the reinforcing member 90 is located at the peripheral edge portion 14B of the conversion layer 14, and the reinforcing member 90 is provided in a region narrower than the region in which the conversion layer 14 covers the first surface 11A of the base material 11.

Rework is a process of removing the flexible cable 112 or a component electrically connected to the base material 11 (the sensor substrate 12) and reconnecting the flexible cable 112 or the component due to problems or displacement. Therefore, by making the reinforcing member 90 smaller than the base material 11, the rework can be performed without being obstructed by the end portion of the reinforcing member 90, so that the rework of the flexible cable 112 can be facilitated.

Figure 11E:
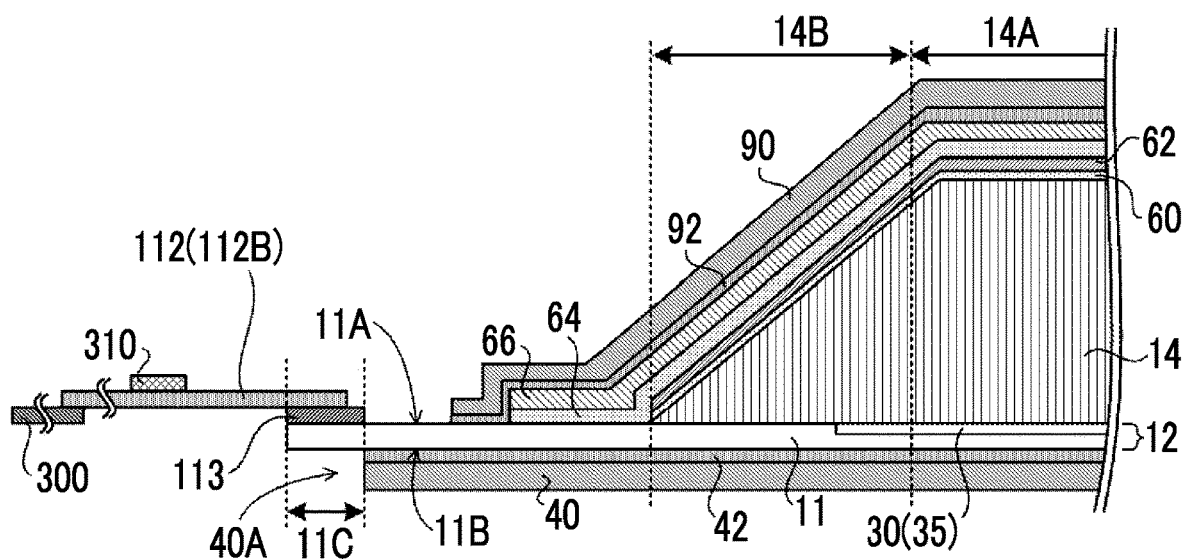
FIG. 11E is a cross-sectional view taken along line A-A of another example of a radiation detector of the Modification Example 1.

In addition, for example, as shown in FIG. 11E, the reinforcing member 90 may be provided in a state of being bent along an inclined surface in the peripheral edge portion 14B of the conversion layer 14. In the example shown in FIG. 11E, the reinforcing member 90 covers a portion where the adhesive layer 64 and the protective layer 66 cover the first surface 11A of the base material 11 and the outer surface of the base material 11 on the first surface 11A. That is, the end portions of the adhesive layer 64 and the protective layer 66 are sealed by the reinforcing member 90. The portion of the reinforcing member 90 extending on the base material 11 is adhered to the base material 11 via the gluing agent 92. By covering the end portions of the adhesive layer 64 and the protective layer 66 with the reinforcing member 90 in this way, peeling of the protective layer 66 can be suppressed.

Modification Example 2

Figure 12:
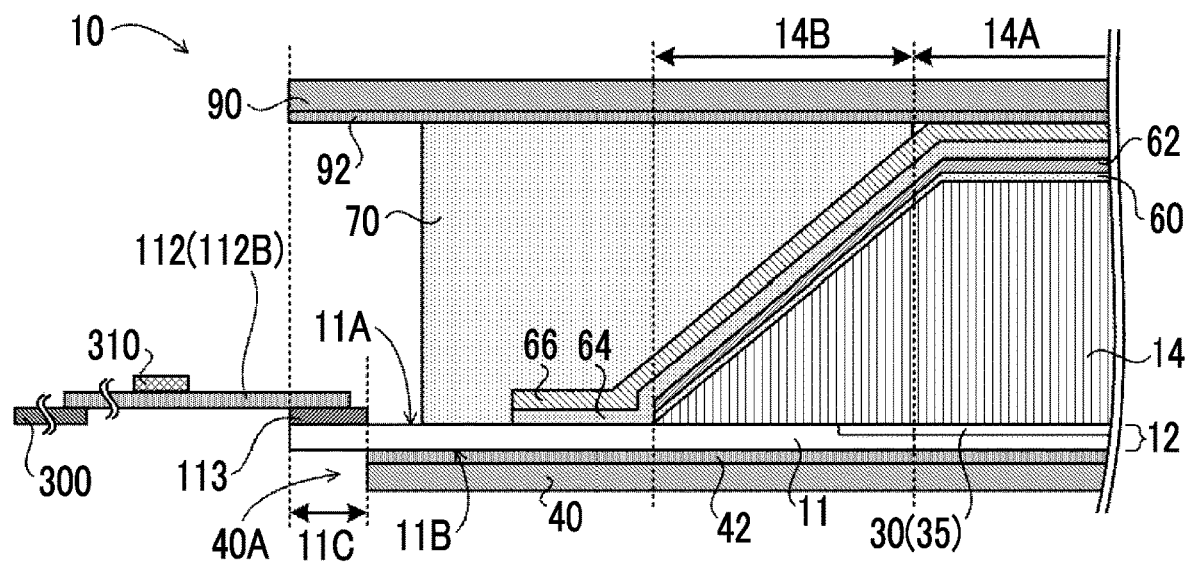
FIG. 12 is a cross-sectional view taken along a line A-A of an example of a radiation detector of the Modification Example 2.

In the present modification example, an aspect in which the periphery of the conversion layer 14 is sealed in the radiation detector 10 will be described with reference to FIG. 12. FIG. 12 shows an example of a cross-sectional view of the radiation detector 10 of the modification example corresponding to cross-sectional view taken along line A-A of the radiation detector 10 shown in FIG. 3A.

As shown in FIG. 12, the peripheral edge portion 14B of the conversion layer 14 may be sealed by a sealing member 70. In the example shown in FIG. 12, the sealing member 70 is provided in the space created by the base material 11, the conversion layer 14, and the reinforcing member 90 as described above. Specifically, in a region corresponding to the peripheral edge portion 14B of the conversion layer 14 and in a region further outside the region, the sealing member 70 is provided in a space formed between the conversion layer 14 (the protective layer 66) and the reinforcing member 90. The material of the sealing member 70 is not particularly limited, and for example, a resin can be used.

The method of providing the sealing member 70 is not particularly limited. For example, on the conversion layer 14 covered with the gluing layer 60, the reflective layer 62, the adhesive layer 64, and the protective layer 66, after the reinforcing member 90 is provided by the gluing agent 92, the space formed between the conversion layer 14 (the protective layer 66) and the reinforcing member 90 may be filled with the sealing member 70 having fluidity to harden the reinforcing member 90. In addition, for example, after the conversion layer 14, the gluing layer 60, the reflective layer 62, the adhesive layer 64, and the protective layer 66 are sequentially formed on the base material 11, the sealing member 70 is formed, and in a state where the gluing layer 60, the reflective layer 62, the adhesive layer 64, and the protective layer 66 cover the conversion layer 14 and the sealing member 70, the reinforcing member 90 may be provided by the gluing agent 92.

In addition, the region in which the sealing member 70 is provided is not limited to the aspect shown in FIG. 12. For example, the entire first surface 11A of the base material 11 may be provided with the sealing member 70, and the terminal 113 to which the flexible cable 112 is electrically connected may be sealed together with the flexible cable 112.

Therefore, by filling the space formed between the conversion layer 14 and the reinforcing member 90 with the sealing member 70 and sealing the conversion layer 14, the peeling of the reinforcing member 90 from the conversion layer 14 can be suppressed. Further, since the conversion layer 14 has a structure of being fixed to the sensor substrate 12 by both the reinforcing member 90 and the sealing member 70, the stiffness of the base material 11 is further reinforced.

Modification Example 3

In the present modification example, with reference to FIG. 13A and FIG. 13B, an aspect in which the reinforcing member 90 in the radiation detector 10 is supported by the supporting member 72 will be described. Each of FIG. 13A to FIG. 13B shows an example of a cross-sectional view of the radiation detector 10 of the present modification example corresponding to cross-sectional view taken along line A-A of the radiation detector 10 shown in FIG. 3A.

Figure 13A:
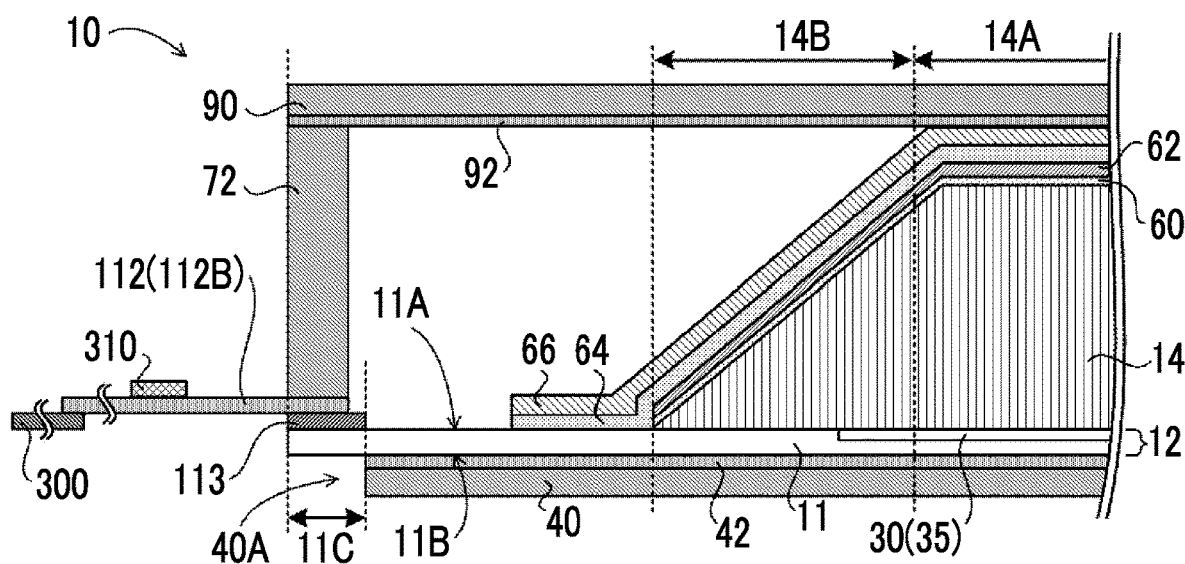
FIG. 13A is a cross-sectional view taken along a line A-A of an example of a radiation detector of the Modification Example 3.

In the radiation detector 10 shown in FIG. 13A, the end portion of the reinforcing member 90 is supported by the supporting member 72. That is, one end of the supporting member 72 is connected to the flexible cable 112 or the first surface 11A of the base material 11, and the other end of the supporting member 72 is connected to the end portion of the reinforcing member 90 by the gluing agent 92. It should be noted that the supporting member 72 may be provided on the entire outer edge portion of the base material 11, or may be provided on a portion of the outer edge portion. By supporting the end portion of the reinforcing member 90 that extends while forming the space between the base material 11 and the reinforcing member 90 by the supporting member 72, it is possible to suppress the conversion layer 14 from peeling off from the sensor substrate 12. Further, by providing the supporting member 72 on the flexible cable 112 connected to the terminal 113, it is possible to suppress the flexible cable 112 from peeling off from the terminal 113.

Figure 13B:
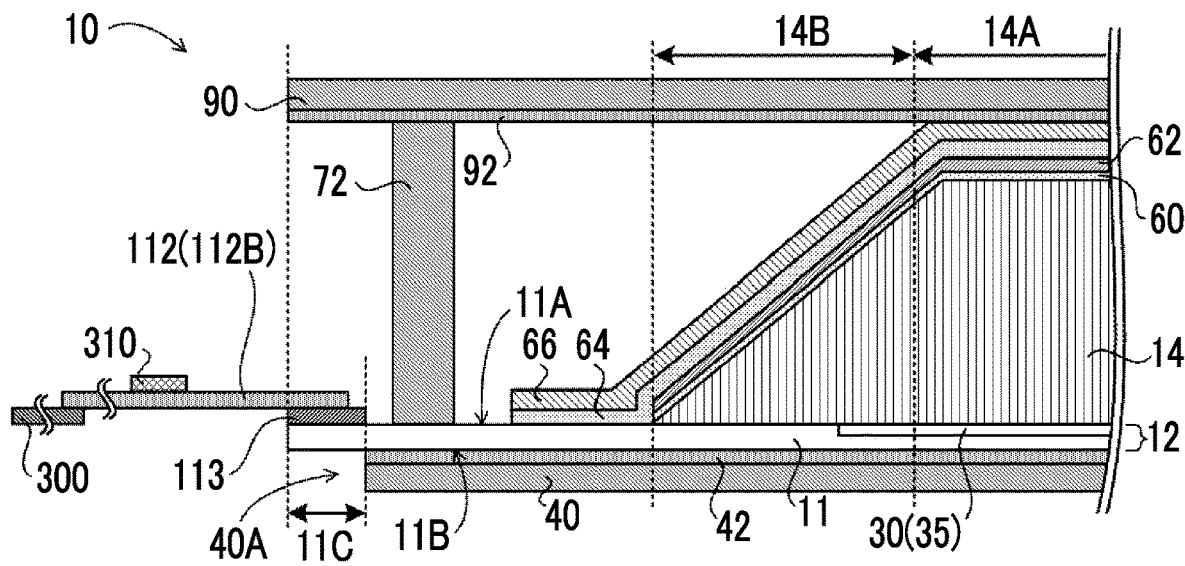
FIG. 13B is a cross-sectional view taken along line A-A of another example of a radiation detector of the Modification Example 3.

On the other hand, in the radiation detector 10 shown in FIG. 13B, a position inside the end portion of the reinforcing member 90 is supported by the supporting member 72. In the example shown in FIG. 13B, the position in which the supporting member 72 is provided is only outside the region in which the flexible cable 112 and the terminal 113 are provided. In the example shown in FIG. 13B, one end of the supporting member 72 is connected to the first surface 11A of the base material 11, and the other end of the supporting member 72 is connected to the end portion of the reinforcing member 90 by the gluing agent 92. Thus, since the flexible cable 112 and the terminal 113 are not provided with the supporting member 72, the rework of the flexible cable 112 can be facilitated.

According to the radiation detector 10 of the present modification example, by supporting the reinforcing member 90 by the supporting member 72, a reinforcing effect of stiffness by the reinforcing member 90 is obtained to the vicinity of the end portion of the base material 11, and the effect of suppressing the bending of the base material 11 can be exerted. Therefore, according to the radiation detector 10 of the present modification example, the peeling of the conversion layer 14 from the sensor substrate 12 can be suppressed.

It should be noted that in a case where the present modification example and the above Modification Example 2 are combined, in other words, the radiation detector 10 comprises the sealing member 70 and the supporting member 72, the sealing member 70 may be filled in a part or the whole of the space surrounded by the supporting member 72, the reinforcing member 90, the conversion layer 14, and the base material 11, and sealed by the sealing member 70.

Modification Example 4

Figure 14:
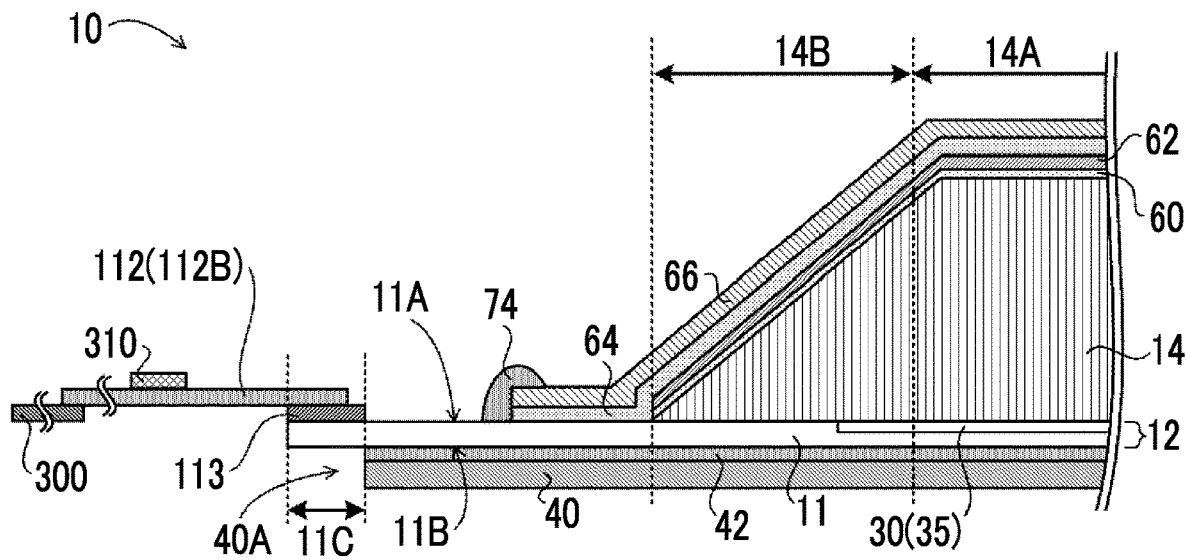
FIG. 14 is a cross-sectional view taken along a line A-A of an example of a radiation detector of the Modification Example 4.

In the present modification example, with reference to FIG. 14, an aspect in which the end portion of the adhesive layer 64 and the protective layer 66 are sealed in the aspect in which the radiation detector 10 does not comprise the reinforcing member 90 will be described. FIG. 14 shows an example of a cross-sectional view of the radiation detector 10 of the modification example corresponding to cross-sectional view taken along line A-A of the radiation detector 10 shown in FIG. 3A.

As shown in FIG. 14, the end portions of the adhesive layer 64 and the protective layer 66 may be sealed by the sealing member 74. The sealing member 74 is preferably provided in a region extending from the first surface 11A of the base material 11 to the surface of the protective layer 66 and not covering the pixel region 35. A resin can be used as the material of the sealing member 74, and a thermoplastic resin is particularly preferable. Specifically, acrylic glue, urethane-based glue, or the like can be used as the sealing member 74. Therefore, according to the radiation detector 10 of the modification example, by sealing the end portions of the adhesive layer 64 and the protective layer 66 with the sealing member 74, the peeling of the adhesive layer 64 and the protective layer 66 can be suppressed.

Modification Example 5

Figure 15:
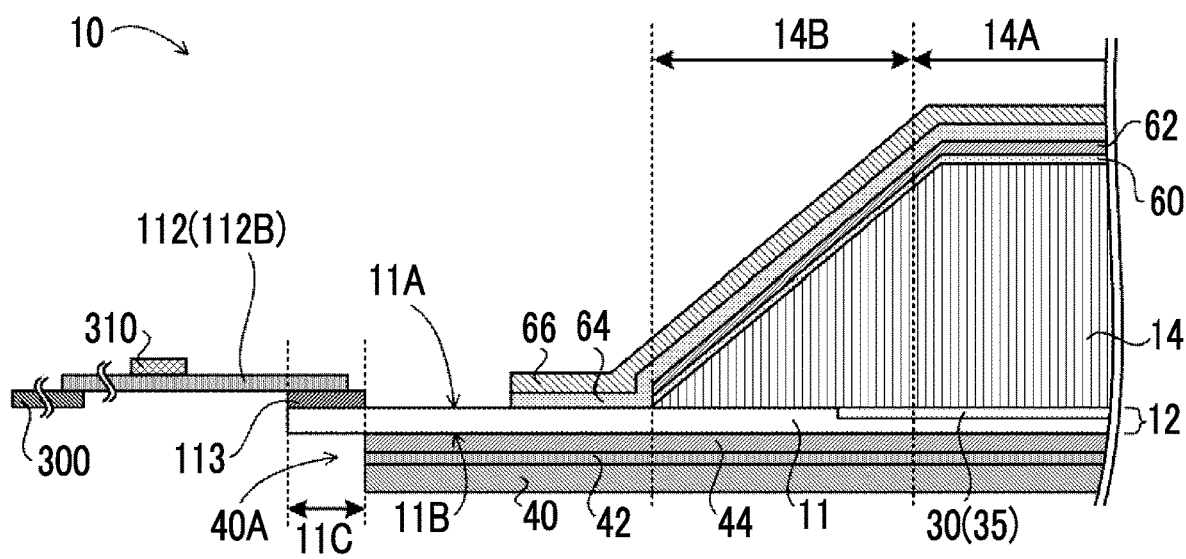
FIG. 15 is a cross-sectional view taken along a line A-A of an example of a radiation detector of the Modification Example 5.

In the present modification example, an aspect in which the radiation detector 10 comprises an antistatic layer 44 will be described with reference to FIG. 15. FIG. 15 shows an example of a cross-sectional view of the radiation detector 10 of the modification example corresponding to cross-sectional view taken along line A-A of the radiation detector 10 shown in FIG. 3A.

As shown in FIG. 15, in the radiation detector 10 of the present modification example, the antistatic layer 44 is provided on the second surface 11B of the base material 11. The reinforcing substrate 40 is provided on a surface of the antistatic layer 44 on the side opposite to a surface on the second surface 11B side by the gluing agent 42. In other words, the reinforcing substrate 40, the gluing agent 42, the antistatic layer 44, and the base material 11 are laminated in this order.

The material of the antistatic layer 44 has the function of suppressing the influence of electromagnetic wave noise and static electricity from the outside. As the antistatic layer 44, for example, a laminated membrane of a resin film such as Alpet (registered trademark) and a metal film, an antistatic paint "Colcoat" (product name: manufactured by Colcoat Co., Ltd.), PET, polypropylene or the like can be used.

It should be noted that the region in which the antistatic layer 44 is provided may be a region that at least covers the pixel region 35, and is not limited to the aspect shown in FIG. 15.

Therefore, according to the radiation detector 10 of the present modification example, since the antistatic layer 44 is provided on the second surface 11B of the base material 11, electromagnetic noise from the outside including the control substrate 110 and the power supply unit 108 can be shielded.

Modification Example 6

In the present modification example, a modification example of a stored state of the radiation detector 10 in the radiography apparatus 1 will be described with reference to FIG. 16A to FIG. 16E. Each of FIG. 16A to FIG. 16E is an example of a cross-sectional view of the radiography apparatus 1 of the present modification example.

Figure 16A:
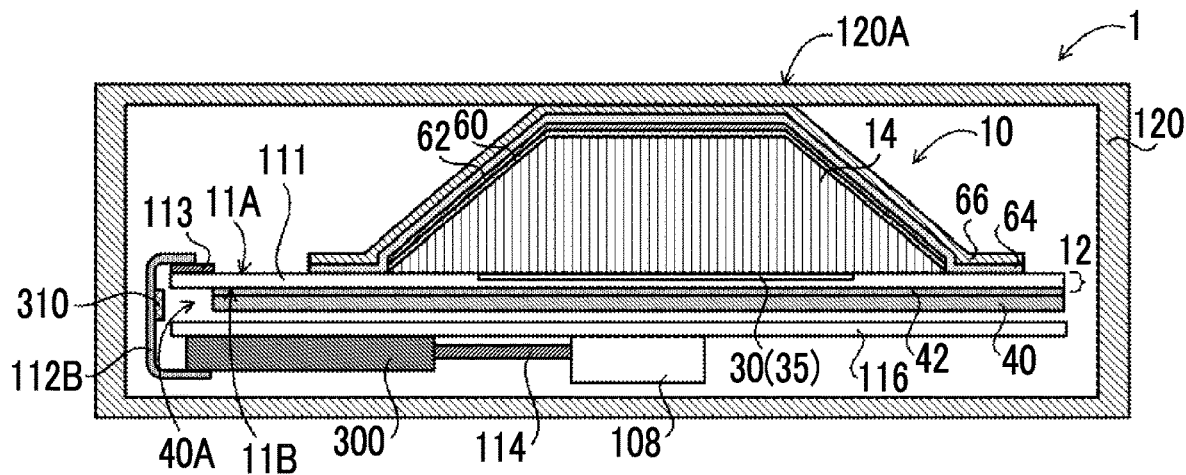
FIG. 16A is a cross-sectional view of an example of a radiography apparatus of the Modification Example 6.

FIG. 16A shows an example of an aspect in which the radiation detector 10 is in contact with the inner wall surface of the top plate on the irradiation surface 120A side of the housing 120. In the example shown in FIG. 16A, the conversion layer 14 is in contact with the inner wall surface of the top plate on the irradiation surface 120A side of the housing 120. It should be noted that in a case where the reinforcing member 90 is comprised as in the Modification Example 1, the radiation detector 10 has an aspect in which the reinforcing member 90 is in contact with the inner wall surface of the top plate on the irradiation surface 120A side of the housing 120.

In this case, the radiation detector 10 and the inner wall surface of the housing 120 may be adhered to each other via an adhesive layer, or may simply be in contact with each other without an adhesive layer. Since the radiation detector 10 and the inner wall surface of the housing 120 are in contact with each other as described above, the stiffness of the radiation detector 10 is further ensured.

Figure 16B:
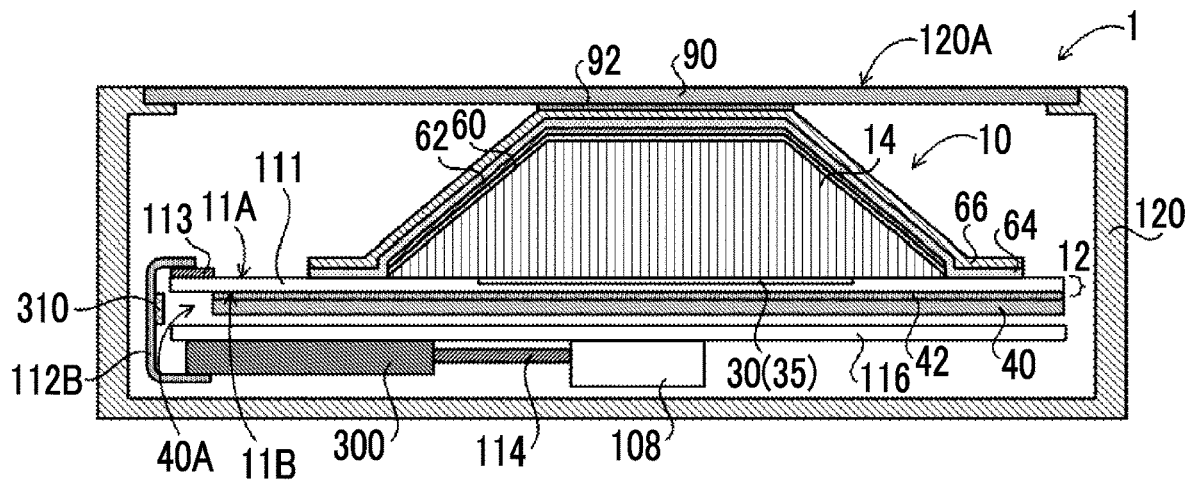
FIG. 16B is a cross-sectional view of another example of the radiography apparatus of the Modification Example 6.

On the other hand, FIG. 16B shows an example of an aspect in which the reinforcing member 90 is adopted as the top plate on the irradiation surface 120A side of the housing 120. In this case, as shown in FIG. 16B, the size of the reinforcing member 90 is larger than that of the sensor substrate 12, and the end portion of the reinforcing member 90 protrudes outward from the end portion of the sensor substrate 12. In the radiography apparatus 1 shown in FIG. 16B, by fitting the reinforcing member 90 into an opening portion of the housing 120 having an opening state in the top plate portion on the irradiation surface 120A side, the radiation detector 10 is housed inside the housing 120. Thus, by using the reinforcing member 90 of the radiation detector 10 as the top plate of the housing 120, a thickness of the housing 120, more specifically, a thickness in a direction through which the radiation passes, can be made smaller, and the radiography apparatus 1 can be made thinner. In addition, since the top plate of the housing 120 itself is unnecessary, the weight of the radiography apparatus 1 can be made lightweight.

Figure 16C:
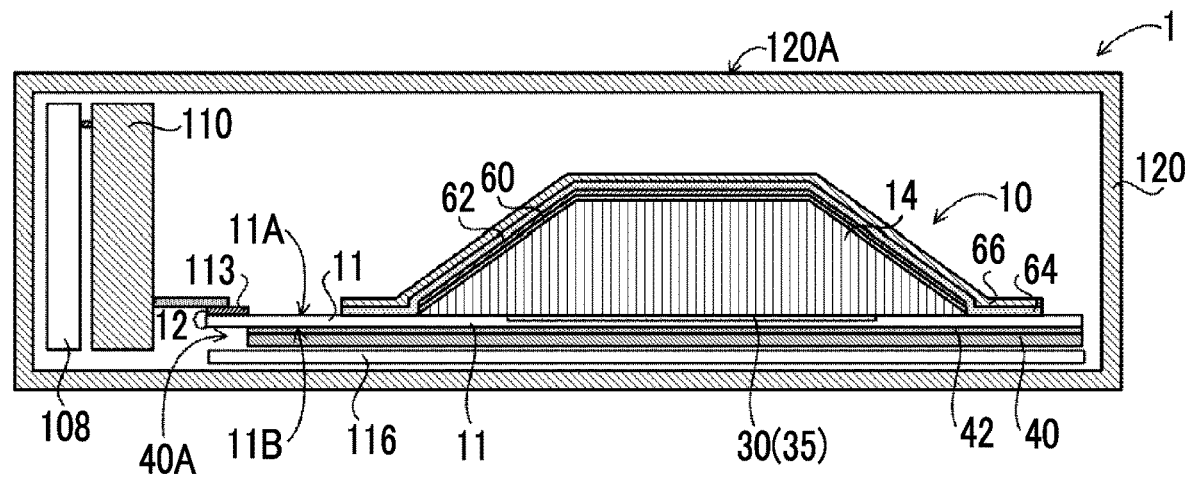
FIG. 16C is a cross-sectional view of another example of the radiography apparatus of the Modification Example 6.

FIG. 16C exemplifies a configuration in which the circuit units such as the radiation detector 10, the control substrate 110, and the power supply unit 108 are juxtapositioned side by side in the lateral direction in the drawing. In other words, in the radiography apparatus 1 shown in FIG. 16C, the radiation detector 10 and the circuit unit are disposed side by side in a direction intersecting the irradiation direction of the radiation.

It should be noted that FIG. 16C shows an aspect in which both the power supply unit 108 and the control substrate 110 are provided on one side of the radiation detector 10, more specifically, on one side of the rectangular pixel region 35, but the positions where the circuit units such as the power supply unit 108 and the control substrate 110 are provided are not limited to the aspect shown in FIG. 16C. For example, the circuit units such as the power supply unit 108 and the control substrate 110 may be provided so as to be dispersed on each of the two sides facing the pixel region 35, or may be provided so as to be dispersed on each of the two adjacent sides. Therefore, by disposing the radiation detector 10 and the circuit unit side by side in the direction intersecting the irradiation direction of the radiation, the thickness of the housing 120, more specifically, the thickness in the direction through which the radiation passes can be made smaller, and the radiography apparatus 1 can be made thinner.

Figure 16D:
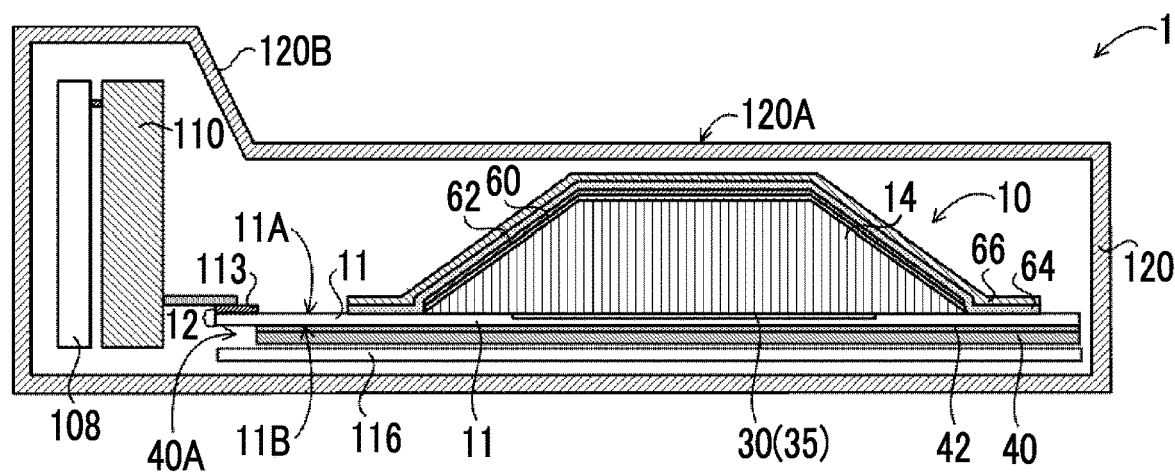
FIG. 16D is a cross-sectional view of another example of the radiography apparatus of the Modification Example 6.

In addition, in a case where the radiation detector 10 and the circuit unit are disposed side by side in the direction intersecting the irradiation direction of the radiation, as shown in FIG. 16D, as in the radiography apparatus 1, the portion of the housing 120 provided with each of the circuit unit such as the power supply unit 108 and the control substrate 110 may have different thickness from the portion of the housing 120 provided with the radiation detector 10.

As shown in the examples shown in FIG. 16C and FIG. 16D, the circuit unit such as the power supply unit 108 and the control substrate 110 may have a thickness larger than that of the radiation detector 10. In such a case, as in the example shown in FIG. 16D, a thickness of a portion of the housing 120 in which the radiation detector 10 is provided may be thinner than a thickness of a portion of the housing 120 in which each of the circuit unit such as the power supply unit 108 and the control substrate 110 is provided. According to the radiography apparatus 1 shown in FIG. 16D, an ultrathin radiography apparatus 1 corresponding to the thickness of the radiation detector 10 can be configured.

As shown in the example shown in FIG. 16D, in a case where the thickness of the portion of the housing 120 in which each of the circuit unit such as the power supply unit 108 and the control substrate 110 is provided and the portion of the housing 120 in which the radiation detector 10 is provided are different from each other, it is preferable that a shape of a boundary portion 120B has an inclination, since there is a concern that a level difference in a boundary portion of both portions may cause a sense of incongruity or the like to an examinee contacting the boundary portion 120B. Further, the portion of the housing 120 in which each of the circuit unit such as the power supply unit 108 and the control substrate 110 is housed and the portion of the housing 120 in which the radiation detector 10 is housed may be formed of different materials.

Figure 16E:
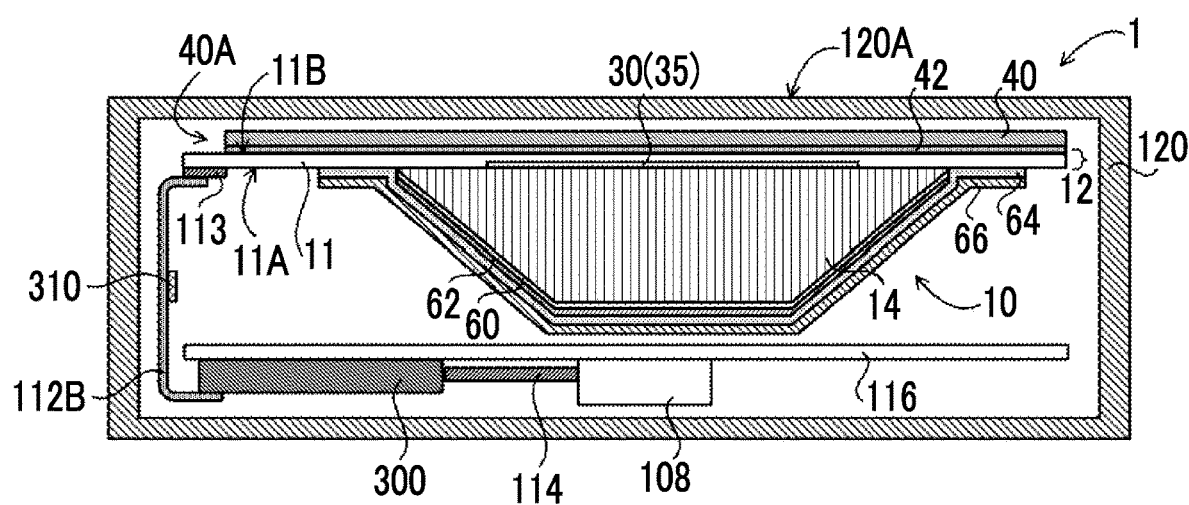
FIG. 16E is a cross-sectional view of another example of the radiography apparatus of the Modification Example 6.

FIG. 16E shows an example of the radiography apparatus 1 in the case where the radiation detector 10 of the present embodiment is applied to an irradiation side sampling (ISS) system in which radiation is irradiated from the second surface 11B side of the base material 11. As described above, the radiation detector 10 of the present embodiment can also be applied to the ISS type radiography apparatus 1.

As described above, each of the above radiation detectors 10 comprises the sensor substrate 12 and the reinforcing substrate 40. In the sensor substrate 12, a plurality of pixels 30 for accumulating the charges generated according to light converted from radiation are formed in the pixel region 35 on the first surface 11A of the flexible base material 11, and the terminal 113 for electrically connecting a flexible cable 112 to the first surface 11A is provided. The reinforcing substrate 40 is provided on the second surface 11B opposite to the first surface 11A of the base material 11 in a region excluding at least the facing region 11C facing the terminal 113 to reinforce the stiffness of the base material 11.

In a case where the terminal 113 is electrically connected to the flexible cable 112, the reinforcing substrate 40 reinforces the bending stiffness of the base material 11 in the vicinity of the terminal 113. On the other hand, the heat applied to the terminal 113 is applied to the base material 11 by the heat treatment performed in a case where the flexible cable 112 is electrically connected to the terminal 113. The heat applied to the base material 11 by this heat treatment mainly tends to propagate from the facing region 11C of the second surface 11B to the reinforcing substrate 40. In a case where the heat propagates to the reinforcing substrate 40, the reinforcing substrate 40 may be deformed by the propagated heat.

However, in each of the above radiation detectors 10, the reinforcing substrate 40 for reinforcing the stiffness of the base material 11 is not provided in the facing region 11C on the second surface 11B of the base material 11. Therefore, the amount of heat propagated to the reinforcing substrate 40 can be reduced, so that deformation of the reinforcing substrate 40 can be suppressed.

Accordingly, in each of the above radiation detectors 10, the bending stiffness is high, and the deformation of the reinforcing substrate 40 due to the heat applied to the terminals can be suppressed.

It should be noted that the configurations of the radiography apparatus 1 and the radiation detector 10 and the manufacturing method thereof are not limited to the aspect described with reference to FIG. 1 to FIG. 16E. For example, an aspect in which the pixels 30 are two-dimensionally arranged in a matrix as shown in FIG. 1 has been described, but the present invention is not limited to this and may be, for example, a one-dimensional array or a honeycomb array. In addition, the shape of the pixel is not limited, and may be rectangular or polygonal such as hexagon. Further, it goes without saying that the shape of the pixel region 35 is not limited.

In addition, the configuration, manufacturing method, and the like of the radiography apparatus 1 and the radiation detector 10 and the like in the above embodiments and each modification example are examples, and it is needless to say that they can be changed in accordance with circumstances within a range not deviating from the gist of the present invention.

What is claimed is:
1. A radiation detector comprising:
   a substrate in which a plurality of pixels for accumulating charges generated according to light converted from radiation are formed in a pixel region on the first surface of a flexible base material, and a terminal for electrically connecting a cable is provided on the first surface; and
   a reinforcing substrate that is provided in a region of a second surface opposite to the first surface of the base material, excluding at least a facing region facing the terminal, to reinforce a stiffness of the base material.
2. The radiation detector according to claim 1, wherein the reinforcing substrate is provided with a cutout portion at a position including the facing region.
3. The radiation detector according to claim 1, wherein the reinforcing substrate is provided with a gap portion at a position including the facing region.

4. The radiation detector according to claim 1,
wherein the reinforcing substrate is provided in a region extending to at least a part of a side provided with the terminal of the base material.

5. The radiation detector according to claim 1,
wherein the substrate is provided with a plurality of the terminals, and
the reinforcing substrate is also provided in a region corresponding to a portion between the plurality of terminals.

6. The radiation detector according to claim 1,
wherein the reinforcing substrate is provided in a region including the facing region, and excluding at least a region in which heat that causes a deformation amount of the reinforcing substrate to be a predetermined amount or more is applied to applied to the base material in a heat treatment performed in a case where the cable is electrically connected to the terminal.

7. The radiation detector according to claim 1,
wherein a bending stiffness of the reinforcing substrate is higher than that of the base material.

8. The radiation detector according to claim 1,
wherein a bending stiffness of the reinforcing substrate is 540 Pacm$^4$ or more and 140,000 Pacm$^4$ or less.

9. The radiation detector according to claim 1, further comprising:
a conversion layer that converts the radiation into light, which is provided in a region including the pixel region on the first surface of the base material and excluding a region in which the terminal is provided; and
the reinforcing member provided on a surface of the conversion layer, which is opposite to a surface on the base material side.

10. A radiography apparatus comprising:
the radiation detector according to claim 1; and
a circuit unit for reading the charges accumulated in the plurality of pixels.

11. A method of manufacturing a radiation detector, the method comprising:
a forming a substrate in which a flexible base material is provided on a support, a plurality of pixels for accumulating charges generated according to light converted from radiation are provided in a pixel region on the first surface of the base material, and a terminal for electrically connecting a cable is provided on the first surface; and
a providing a reinforcing substrate for reinforcing a stiffness of the base material in a region of a second surface opposite to the first surface of the base material, excluding at least a facing region facing the terminal.

12. The method of manufacturing the radiation detector according to claim 11, further comprising an electrically connecting the cable to the terminal after providing the reinforcing substrate.

13. The method of manufacturing the radiation detector according to claim 11, further comprising:
a providing a replenishing member having a smaller deformation amount with respect to heat than that of the reinforcing substrate in a region in which the reinforcing substrate is not provided on the second surface of the base material; and
an electrically connecting the cable to the terminal after providing the reinforcing substrate and the replenishing member.

14. The method of manufacturing the radiation detector according to claim 13, the method further comprising a removing the replenishing member after electrically connecting the cable to the terminal.

15. The method of manufacturing the radiation detector according to claim 11, further comprising:
a providing a replenishing member having a higher thermal conductivity than that of the reinforcing substrate in a region in which the reinforcing substrate is not provided on the second surface of the base material; and
an electrically connecting the cable to the terminal after providing the reinforcing substrate and the replenishing member.

16. The method of manufacturing the radiation detector according to claim 15, the method further comprising a removing the replenishing member after electrically connecting the cable to the terminal.

* * * * *